(12) United States Patent
Lee et al.

(10) Patent No.: US 10,660,534 B2
(45) Date of Patent: May 26, 2020

(54) METHOD, APPARATUS, AND SYSTEM PROVIDING EXERCISE GUIDE INFORMATION

(71) Applicant: Samsung Electronics Co., Ltd., Suwon-si (KR)

(72) Inventors: Choonghee Lee, Seoul (KR); Byunghoon Ko, Hwaseong-si (KR); SangKon Bae, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 837 days.

(21) Appl. No.: 14/919,976

(22) Filed: Oct. 22, 2015

(65) Prior Publication Data
US 2016/0213979 A1    Jul. 28, 2016

(30) Foreign Application Priority Data

Jan. 26, 2015 (KR) .................. 10-2015-0012111

(51) Int. Cl.
*A61B 5/024* (2006.01)
*G09B 19/00* (2006.01)
*G06F 19/00* (2018.01)
*A61B 5/00* (2006.01)

(52) U.S. Cl.
CPC ...... *A61B 5/02438* (2013.01); *G06F 19/3481* (2013.01); *G09B 19/0038* (2013.01); *A61B 5/0002* (2013.01); *A61B 2503/10* (2013.01); *A61B 2562/0219* (2013.01)

(58) Field of Classification Search
CPC ............ G09B 19/0038; G06F 19/3481; A61B 2503/10; A61B 2562/0219; A61B 5/0002; A61B 5/02438
See application file for complete search history.

(56) References Cited

U.S. PATENT DOCUMENTS

| | | | |
|---|---|---|---|
| 9,682,306 B2 * | 6/2017 | Lin | .................... A63B 71/0619 |
| 2009/0069156 A1 | 3/2009 | Kurunmaki et al. | |
| 2009/0286657 A1 * | 11/2009 | Sveshnikov | ....... G09B 19/0038 482/92 |
| 2009/0312656 A1 * | 12/2009 | Lau | .................... A61B 5/02438 600/509 |
| 2010/0216601 A1 | 8/2010 | Saalasti et al. | |
| 2011/0082397 A1 * | 4/2011 | Alberts | .................... A61H 1/02 601/26 |
| 2012/0035021 A1 | 2/2012 | Saalasti et al. | |

(Continued)

FOREIGN PATENT DOCUMENTS

| JP | 3567561 B2 | 6/2004 |
|---|---|---|
| KR | 10-2004-0106648 A | 12/2004 |

(Continued)

*Primary Examiner* — Eddy Saint-Vil
(74) *Attorney, Agent, or Firm* — NSIP Law

(57) ABSTRACT

A method of providing exercise guide information that may include receiving a biosignal including a heart rate of a user, obtained through a wearable device, and a rate of perceived exertion (RPE), as indicated by the user, with respect to an exercise of a current order, and providing exercise guide information to the user according to a determined exercise intensity of the user in the current order that is based on the received biosignal and RPE.

32 Claims, 14 Drawing Sheets

(56) References Cited

U.S. PATENT DOCUMENTS

| | | | |
|---|---|---|---|
| 2012/0214644 A1* | 8/2012 | Sasaki | G06F 19/3481 482/3 |
| 2013/0053990 A1* | 2/2013 | Ackland | G06Q 30/02 700/91 |
| 2014/0073486 A1* | 3/2014 | Ahmed | A61B 5/02405 482/9 |
| 2015/0165271 A1* | 6/2015 | Lin | A61B 5/024 482/9 |
| 2015/0251074 A1* | 9/2015 | Ahmed | A61B 5/02405 700/91 |

FOREIGN PATENT DOCUMENTS

| | | |
|---|---|---|
| KR | 10-2008-0022680 A | 3/2008 |
| KR | 10-2012-0033898 A | 4/2012 |

* cited by examiner

1300

1400

METHOD, APPARATUS, AND SYSTEM PROVIDING EXERCISE GUIDE INFORMATION

CROSS-REFERENCE TO RELATED APPLICATION(S)

This application claims the benefit under 35 USC 119(a) of Korean Patent Application No. 10-2015-0012111, filed on Jan. 26, 2015, in the Korean Intellectual Property Office, the entire disclosure of which is incorporated herein by reference for all purposes.

BACKGROUND

1. Field

The following description relates to a method, apparatus, and system providing exercise guide information.

2. Description of Related Art

In general, an exercise management program may evaluate a training effect based on a user's oxygen consumption and suggests an exercise intensity to the user. The oxygen consumption may be estimated based on personal body information of the user and heart rate information measured through a sensor attached to the user's body.

In this example, expended calories and excess post-exercise oxygen consumption (EPOC) may be obtained based on the estimated oxygen consumption. However, since such oxygen consumption values are generalized values that are estimated through a neural network, the values may be inaccurate when considering the individual characteristics of each user. Further, users have different heart rates and different heartbeat patterns. Thus, for example, an inaccurate exercise intensity may be suggested to a user when only generalized values are used in estimating the oxygen consumption. In a worst case, if an inaccurate exercise intensity is suggested to the user, the user may go into shock due to excessive exercising.

SUMMARY

This Summary is provided to introduce a selection of concepts in a simplified form that are further described below in the Detailed Description. This Summary is not intended to identify key features or essential features of the claimed subject matter, nor is this Summary intended to be used as an aid in determining the scope of the claimed subject matter.

One or more embodiments include a method providing exercise guide information, the method including receiving a biosignal that includes a heart rate of a user obtained through a wearable device, receiving a rate of perceived exertion (RPE), as indicated by the user, with respect to an exercise of a current order, determining, using at least one processing device, an exercise intensity of the user in the current order based on the received biosignal and the received RPE, and providing exercise guide information to the user based on the determined exercise intensity.

The receiving of the biosignal may include wirelessly receiving, from the wearable device, at least one of biosignals of the user sensed before the exercise of the current order, biosignals of the user sensed during the exercise of the current order, and biosignals of the user sensed within a predetermined time period after the exercise of the current order.

The method may further include calculating initial exercise guide information to achieve an exercise goal based on received personal information.

The method may further include receiving the personal information from the user, the personal information including at least one of an exercise type, the exercise goal, and body information of the user.

The initial exercise guide information may include at least one of an initial exercise intensity, a target heart rate, and an exercise duration to achieve the exercise goal based on a user indicated exercise type.

The determining of the exercise intensity may include calculating a difference between the target heart rate and the heart rate of the user, comparing a result of the calculating to a preset threshold, and determining the exercise intensity of the user in the current order based on a result of the comparing and the received RPE.

The method may further include matching the result of the calculating of the difference between the target heart rate and the heart rate of the user, the result of the comparing, and the received RPE, and storing a result of the matching in an exercise history library.

The determining of the exercise intensity may include applying a respective preset weight to each of the result of the comparing and the received RPE, calculating an evaluation score of a result of the applying of the respective preset weight, and determining the exercise intensity of the user in the current order based on the calculated evaluation score.

The method may further include determining a target heart rate for an exercise of a next order of the user based on the determined exercise intensity.

The providing of the exercise guide information to the user may include providing the exercise guide information for at least one of the current order and a next order based on the determined exercise intensity.

One or more embodiments include a method providing exercise guide information, the method including receiving one of a rate of perceived exertion (RPE), as indicated by a user, with respect to an exercise of a current order and a biosignal that includes a heart rate of the user, estimating, using at least one processing device, one of biometric data corresponding to the received RPE and an RPE corresponding to the received biosignal using an exercise history library containing cumulative information associated with an exercise by the user of a previous order, determining an exercise intensity of the user in the current order based on a result of the estimating, and providing exercise guide information to the user based on the determined exercise intensity.

The method may further include receiving or maintaining the exercise history library.

The exercise history library may contain at least one of exercise records for exercises of previous orders, average heart rate information including an average cumulative value of differences between target heart rates in the exercises of the previous orders and respective heart rate of the user, a result of comparing the average heart rate information to a preset threshold, and respective RPE of the user corresponding to the result of the comparing.

The estimating may include searching for a biosignal corresponding to the received RPE in the exercise history library, and estimating a biosignal of the user in the current order based on a result of the searching.

The estimating may include searching for an RPE corresponding to the received biosignal in the exercise history library, and estimating the RPE of the user in the current order based on a result of the searching.

One or more embodiments include a method of providing exercise guide information, the method including analyzing an exercise pattern of a user that includes an exercise duration and an exercise speed of the user in a current order, estimating, using at least one processing device, a rate of perceived exertion (RPE) and a biosignal corresponding to the exercise pattern using an exercise history library that contains cumulative information associated with an exercise of a previous order, determining an exercise intensity of the user in the current order based on a result of the estimating, and providing exercise guide information to the user based on the determined exercise intensity.

The estimating may include searching, in the exercise history library, for at least one of an RPE and biosignal based on the exercise pattern, and estimating the RPE and the biosignal corresponding to the exercise pattern based on a result of the searching.

The method may further include receiving the exercise speed of the user from an accelerometer or an exercise quantity measuring apparatus.

The estimating may include searching for an exercise record corresponding to the exercise speed using at least one of the exercise history library and statistics, and estimating the RPE and biosignal corresponding to the exercise pattern based on the exercise record and the exercise history library.

One or more embodiments include a non-transitory computer-readable storage medium including computer readable code to cause at least one processing device to perform one or more of the methods described herein.

One or more embodiments include an apparatus configured to provide exercise guide information, the apparatus including a communicator configured to receive a biosignal that includes a heart rate of a user obtained through a wearable device, a touch display configured to display potential exercise intensities with respect to an exercise of a current order as a plurality of levels, and receive an input to the touch display indicating a level, of the displayed potential exercise intensities, identifying a rate of perceived exertion (RPE) perceived by the user, and a processor configured to determine an exercise intensity of the user in the current order based on the received biosignal and the RPE, and provide exercise guide information to the user with respect to the current order or a next order based on the determined exercise intensity.

The processor may be configured to calculate a difference between a target heart rate and the heart rate of the user, compare a result of the calculating to a preset threshold, and determine the exercise intensity of the user in the current order based on a result of the comparing and the RPE.

The apparatus may further include a storage configured to store an exercise history library in which the result of comparing and the RPE are matched and stored.

One or more embodiments include an apparatus configured to provide exercise guide information, the apparatus including a communicator configured to receive one of a rate of perceived exertion (RPE), as indicated by a user, with respect to an exercise of a current order and a biosignal including a heart rate of the user, a storage including an exercise history library containing cumulative information associated with an exercise of a previous order, and at least one processing device configured to estimate one of biometric data corresponding to the received RPE and an RPE corresponding to the received biosignal using the exercise history library, determine an exercise intensity of the user in the current order based on a result of the estimating, and provide exercise guide information to the user based on the determined exercise intensity.

The exercise history library may contain at least one of exercise records for exercises of previous orders, average heart rate information including an average cumulative value of differences between target heart rates in the exercises of the previous orders and respective heart rate of the user, a result of comparing the average heart rate information to a preset threshold, and respective RPE of the user corresponding to the result of the comparing.

The processor may be configured to estimate a biosignal of the user in the current order based on a biosignal found, with respect to the received RPE, in the exercise history library, and to estimate the RPE corresponding to the received biosignal in the current order based on an RPE found, with respect to the received biosignal, in the exercise history library.

One or more embodiments include an apparatus configured to provide exercise guide information, the apparatus including a storage including an exercise history library containing cumulative information associated with an exercise of a previous order, and a processor configured to analyze an exercise pattern including an exercise duration and an exercise speed of a user in a current order, determine an exercise intensity of the user in the current order based on an estimated rate of perceived exertion (RPE) and estimated biosignal of the current order, both estimated with respect to the exercise pattern using the exercise history library, and provide exercise guide information to the user based on the determined exercise intensity.

The processor may be configured to search for at least one of an RPE and a biosignal corresponding to the exercise pattern in the exercise history library, and estimate the RPE and the biosignal of the current order based on a result of the searching.

The apparatus may further include a communicator configured to receive the exercise speed measured by an accelerometer, configured to measure the exercise speed of the user, or an exercise quantity measuring apparatus.

The apparatus may further include the accelerometer, with the communicator being configured to receive the exercise speed measured by the accelerometer.

The processor may be configured to search for an exercise record corresponding to the exercise speed using at least one of the exercise history library and statistics, and estimate the RPE and biosignal of the current order based on the exercise record and the exercise history library.

One or more embodiments include a system configured to provide exercise guide information, the system including a wearable device configured to sense a biosignal that includes a heart rate of a user, and a mobile device configured to receive the biosignal and a rate of perceived exertion (RPE), as indicated by the user, with respect to an exercise of a current order, and provide exercise guide information to the user according to a determined exercise intensity of the user in the current order that is based on the received biosignal and the received RPE.

Other features and aspects will be apparent from the following detailed description, the drawings, and the claims.

Figure 1:
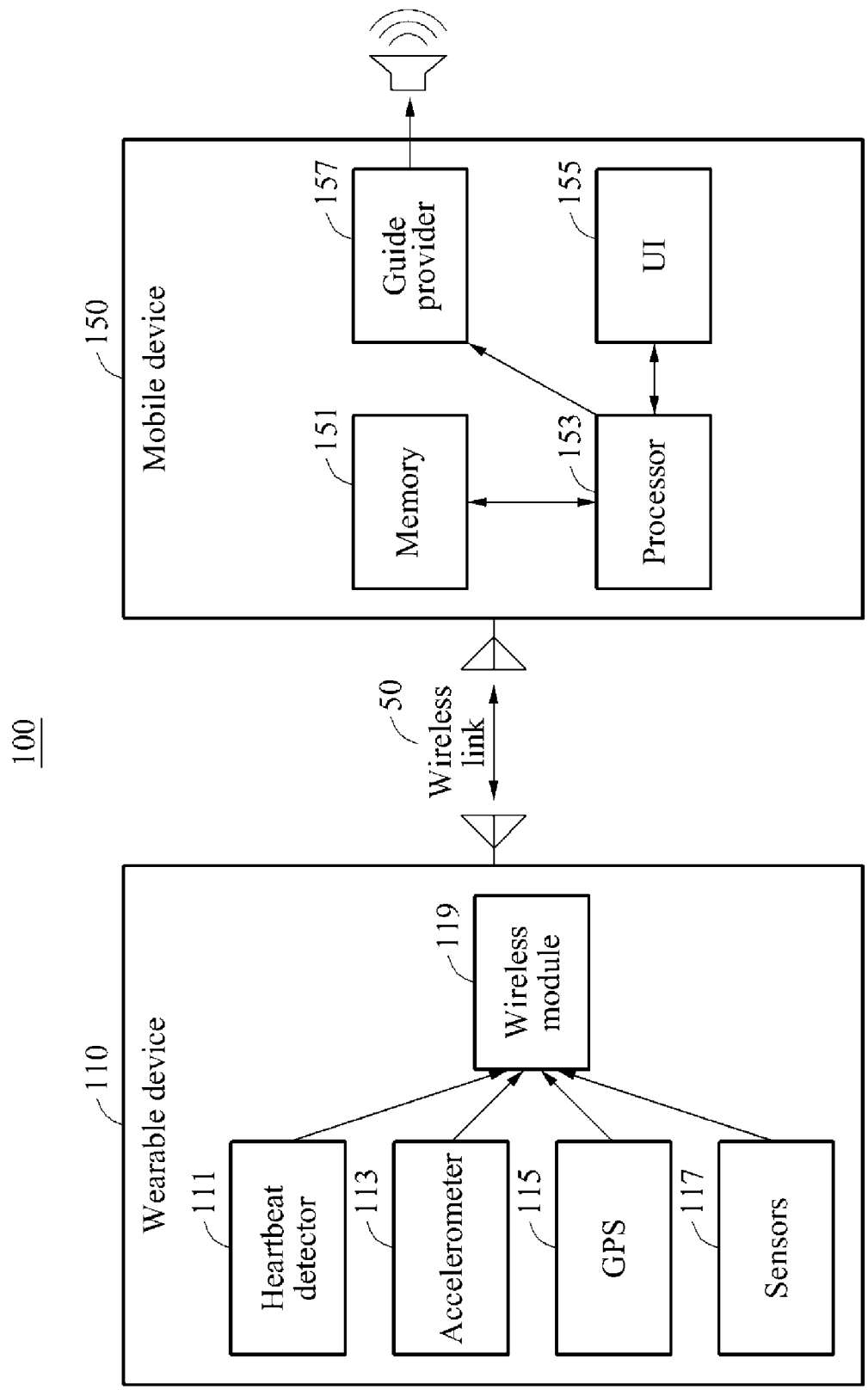
FIG. 1 is a diagram illustrating an example of a system configured to provide exercise guide information, according to one or more embodiments.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, after an understanding of the present disclosure, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that may be well known to one of ordinary skill in the art may be omitted for increased clarity and conciseness.

The features described herein may be embodied in different forms, and are not to be construed as being limited to the examples described herein.

Various alterations and modifications may be made to example embodiments, some of which will be illustrated in detail in the drawings and detailed description. However, it should be understood that these embodiments are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

Unless otherwise defined, all terms including technical and scientific terms used herein have the same meaning as commonly understood by one of ordinary skill in the art to which examples belong, in view of the present disclosure. It will be further understood that terms, such as those defined in commonly-used dictionaries, should be interpreted as having a meaning that is consistent with their meaning in the context of the relevant art and the present disclosure and will not be interpreted in an idealized or overly formal sense unless expressly so defined herein.

Hereinafter, exemplary embodiments will be described in detail with reference to the accompanying drawings, wherein like reference numerals refer to like elements throughout. When it is determined detailed description related to a related known function or configuration may make a purpose of an embodiment unnecessarily ambiguous in describing the embodiment, the detailed description may be omitted accordingly.

FIG. 1 is a diagram illustrating an example of a system configured to provide exercise guide information, according to one or more embodiments.

Referring to FIG. 1, a system 100 configured to provide exercise guide information, hereinafter referred to as the "providing system" 100, may include a wearable device 110 and a mobile device 150, for example.

In this embodiment, the wearable device 110 and the mobile device 150 may connect to each other through a wireless link 50.

For example, the wearable device 110 and the mobile device 150 may include wireless Internet interfaces such as a wireless local area network (WLAN), a wireless fidelity (Wi-Fi) direct, a digital living network alliance (DLNA), a wireless broadband (WiBro), a world interoperability for microwave access (WiMAX), and a high speed downlink packet access (HSDPA), for example, and short-range communication interfaces such as Bluetooth™, a radio frequency identification (RFID), an infrared data association (IrDA), a ultra wideband (UWB), ZigBee, and a near field communication (NFC), noting that alternatives are also available.

The wearable device 110 may include a heartbeat detector 111, an accelerometer 113, a global positioning system (GPS) 115, and sensors 117, for example. The wearable device 110 may be a wrist worn device having a shape of, for example, a watch or a bracelet, or some other wearable device.

The term "heart rate" used herein may refer to a "number of heartbeats", e.g., a number of heartbeats within a minute.

The wearable device 110 may sense a biosignal including a heart rate of a user using the heartbeat detector 111 and the sensors 117, for example. In an embodiment, the heartbeat detector 111 may include a photoplethysmogram (PPG) sensor, noting that such a sensor and/or other types of heart detecting sensors are also available.

The accelerometer 113 may sense an exercise speed of the user that is performing an exercise and wearing the wearable device 110.

The GPS 115 may sense a position of the user that is performing an exercise and wearing the wearable device 110. For example, the mobile device 150 may calculate or determine an exercise quantity with respect to a moving distance of the user based on information on the position of the user received through the wearable device 110.

The wearable device 110 may monitor, in real time, exercise state information of the user including heart rate, acceleration, position information, and other biosignals. Such information may be transmitted to the mobile device 150 through Bluetooth, WiFi, ZigBee, or a customized communication channel to which a security function provided by a wireless module 119 is applied, as only non-limiting examples.

The mobile device 150 may provide an exercise guide with respect to a current exercise intensity of the user, e.g., for an exercise of a current order, based on the exercise state information, and may recommend an exercise intensity for a next order by evaluating the exercise of a current order after the exercise is performed.

The exercise intensity for the next order may be recommended based on a rate of perceived exertion (RPE) indicated with respect to the user's perception of the exercise intensity of the current order. Thus, with consideration of the RPE, an exercise willpower, an exercise objective, and an actual physical strength of each user may be reflected in an exercise guide for a next order.

By iteratively performing a process of recommending the exercise intensity for a next order based on the RPE perceived by the user with respect to the exercise intensity of a current order, an exercise history of the user may be accumulated and reflected and thus, over time, customized exercise guide information optimized for the user may be provided in real time.

The mobile device 150 may be implemented as, for example, a tablet computer, a smart phone, or a personal digital assistance (PDA), as only examples. Further, the mobile device 150 may be a network device such as a server. The mobile device 150 may be a single server computer or a system similar thereto, or at least one server bank or server clouds distributed at different geographical positions, also only as examples.

The mobile device 150 may receive a biosignal sensed through the wearable device 110 or other measuring apparatuses. Further, the mobile device 150 may receive an indication by the user of an RPE perceived by the user with respect to an exercise of a current order.

The mobile device 150 may provide exercise guide information to the user based on the exercise intensity of the user in the current order, evaluated/determined based on the biosignal and the RPE.

For example, it may be assumed that the user performed exercises of a first order, a second order, and a third order, and is currently performing an exercise of a fourth order. In this example, the exercises of the first order, the second order, and the third order performed by the user may be referred to as "exercises of previous orders", and the exercise of the fourth order currently being performed by the user may be referred to as an "exercise of a current order". Further, an exercise of a fifth order to be performed by the user after the exercise of such a fourth order will be referred to as an "exercise of a next order", for example.

The mobile device 150 may include a memory 151, a processor 153, a user interface (UI) 155, and a guide provider 157, for example.

The memory 151 may store an exercise history library containing cumulative information associated with an exercise of a previous order. The exercise history library may contain exercise records for exercises of previous orders, average heart rate information including an average cumulative value of differences between target heart rates in the exercises of the previous orders and the respective heart rate of the user, a result of comparing such average heart rate information to a preset threshold, and a respective RPE of the user corresponding to the result of comparing.

The processor 153 may evaluate an exercise intensity of the user in the current order based on at least one of the received biosignal and the RPE.

For example, the processor 153 may evaluate the exercise intensity of the user in the current order based on, using the exercise history library, a result of estimating one of biometric data corresponding to the received RPE and an RPE corresponding to the received biosignal.

Further, the processor 153 may analyze or determine an exercise pattern including an exercise duration and an exercise speed of the user in the current order, and evaluate the exercise intensity of the user in the current order based on an estimated biosignal and an estimated RPE, e.g., both estimated with respect to the exercise pattern using the exercise history library.

The processor 153 may provide exercise guide information for the current order or a next order based on the exercise intensity evaluated with respect to the exercise of the current order.

The UI 155 may receive an indication of the RPE, as perceived by the user, with respect to the exercise of the current order in various forms. The RPE may be input into the mobile device 150 through the UI 155 in various forms such as any, or any combination, of a touch input of the user with respect to a touch display, a voice input of the user through a microphone, a level of tilting or shaking with respect to a motion of tilting or shaking the mobile device 150 in a horizontal or vertical direction, and a gesture of the user photographed through a photographing device, for example.

Figure 6:
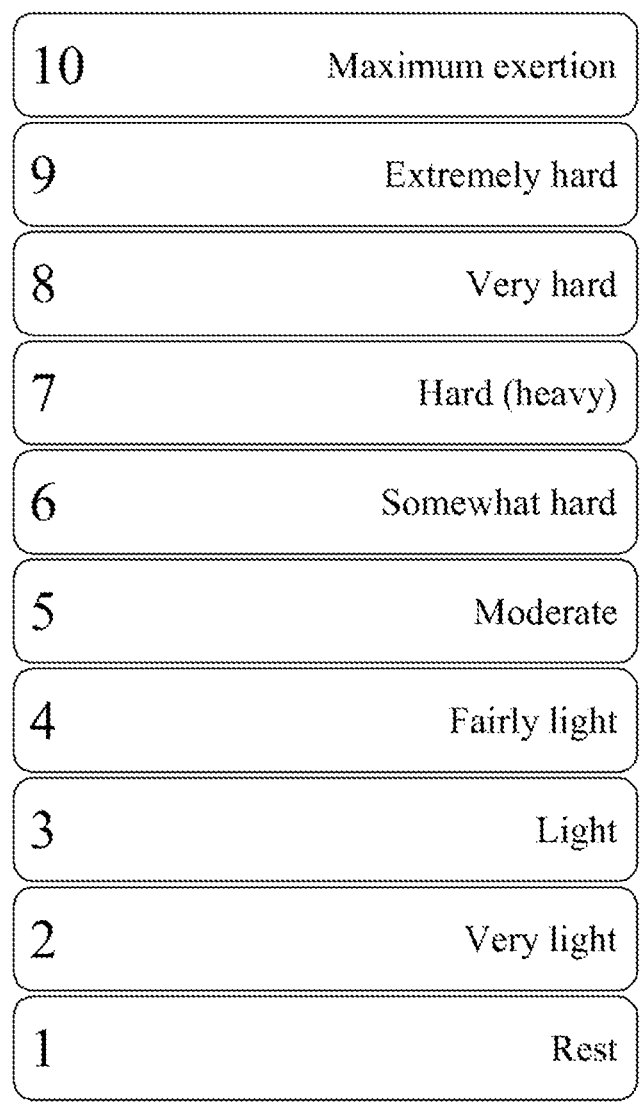
FIG. 6 illustrates an example of a screenshot of a touch display configured to receive a rate of perceived exertion (RPE) perceived by a user, according to one or more embodiments.

The potential RPE may be displayed on the touch display, for example, in a form of a plurality of levels with respect to an exercise intensity. The user may input or select the appropriate RPE by selecting an exercise level perceived by the user through a touch of the touch display. An example of a screenshot of a touch display through which an RPE is input is illustrated in FIG. 6. The touch display may be replaced with a flexible display.

Figure 7:
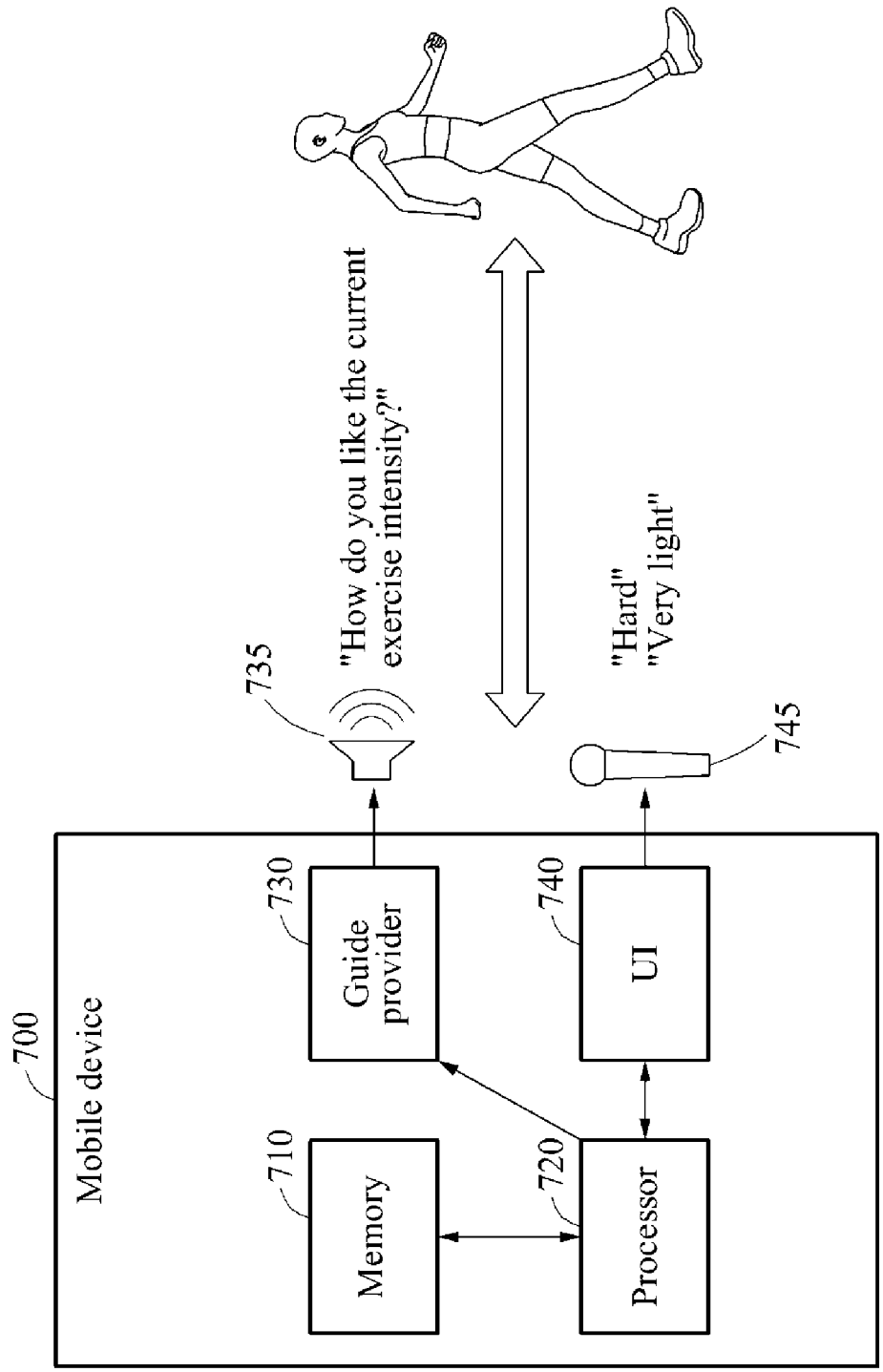
FIG. 7 is a diagram illustrating an example of receiving an RPE perceived by a user using a voice, according to one or more embodiments.

Further, the RPE may be provided to the mobile device 150, for example, through a voice input of the user. An example of a mobile device receiving an RPE through a voice input is illustrated in FIG. 7.

The guide provider 157 may transmit the exercise guide information provided by the processor 153 to the user in a form of an audio guide or a vibration. The guide provider 157 may further include a speaker.

The exercise guide information may be an audio guide saying, for example, "Keep the pace", "Increase the pace", or "Slow down". Further, the exercise guide information may be provided, for example, in a form of a single vibration in a case in which the pace is to be increased, in a form of two vibrations in a case in which the current pace is to be maintained, or in a form of three vibrations in a case in which the pace is to be reduced.

An apparatus for providing exercise guide information to be described hereinafter may be embedded and operate in the mobile device 150, or may be implemented by the mobile device 150.

An environment in which the wearable device 110 and the mobile device 150 are used together is described. However, in an example, the wearable device 110 or the mobile device 150 may perform the foregoing functions independently.

Figure 2:
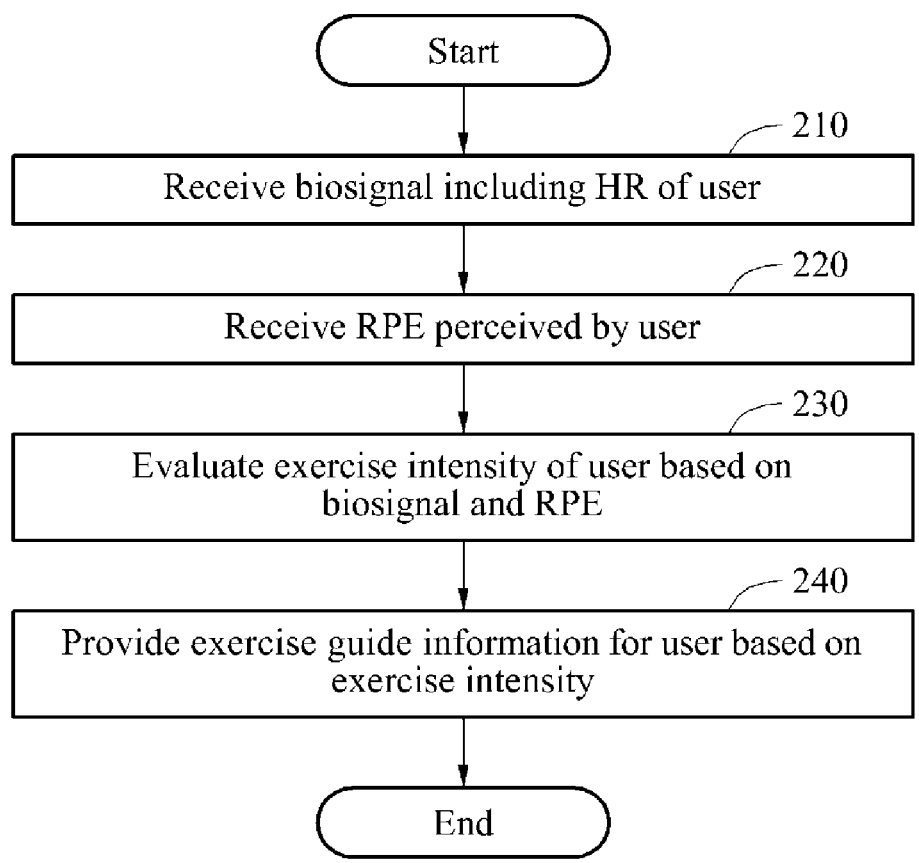
FIG. 2 is a flowchart illustrating an example of a method providing exercise guide information, according to one or more embodiments.

FIG. 2 is a flowchart illustrating an example of a method providing exercise guide information, according to one or more embodiments.

Referring to FIG. 2, an example of providing exercise information based on a heart rate measured by a wearable device or other measuring apparatuses and an RPE perceived by a user is illustrated.

In operation 210, a biosignal including a heart rate of a user obtained through the wearable device may be received. As only an example, the providing apparatus of FIG. 1 may receive at least one of biosignals of the user sensed by the wearable device or the other measuring apparatuses before an exercise of a current order, during the exercise of the current order, and/or within a predetermined time period after the exercise of the current order.

In operation 220 an RPE perceived by the user with respect to the exercise of the current order may be received. As only an example, the providing apparatus may display potential exercise intensities with respect to the exercise of the current order in a form of a plurality of levels on a touch display, as shown in FIG. 6. The user may input or select an RPE corresponding to an exercise intensity perceived by the user by selecting one of the plurality of levels displayed on the touch display.

In operation 230, an exercise intensity of the user in the current order may be evaluated/determined, e.g., by the providing apparatus, based on the biosignal received in operation 210 and the RPE received in operation 220.

In an example, the providing apparatus may score the RPE and reflect the scored RPE in determining a target heart rate for a next order. The RPE may be an index which reflects an actual physical strength and an exercise willpower of the particular user as a subjective cognitive exercise evaluation by the user.

In operation 240, exercise guide information may be provided, e.g., by the providing apparatus, to the user based on the exercise intensity evaluated in operation 230. In this example, the provided exercise guide information may be exercise guide information for the current order or a next or future order.

Figure 3:
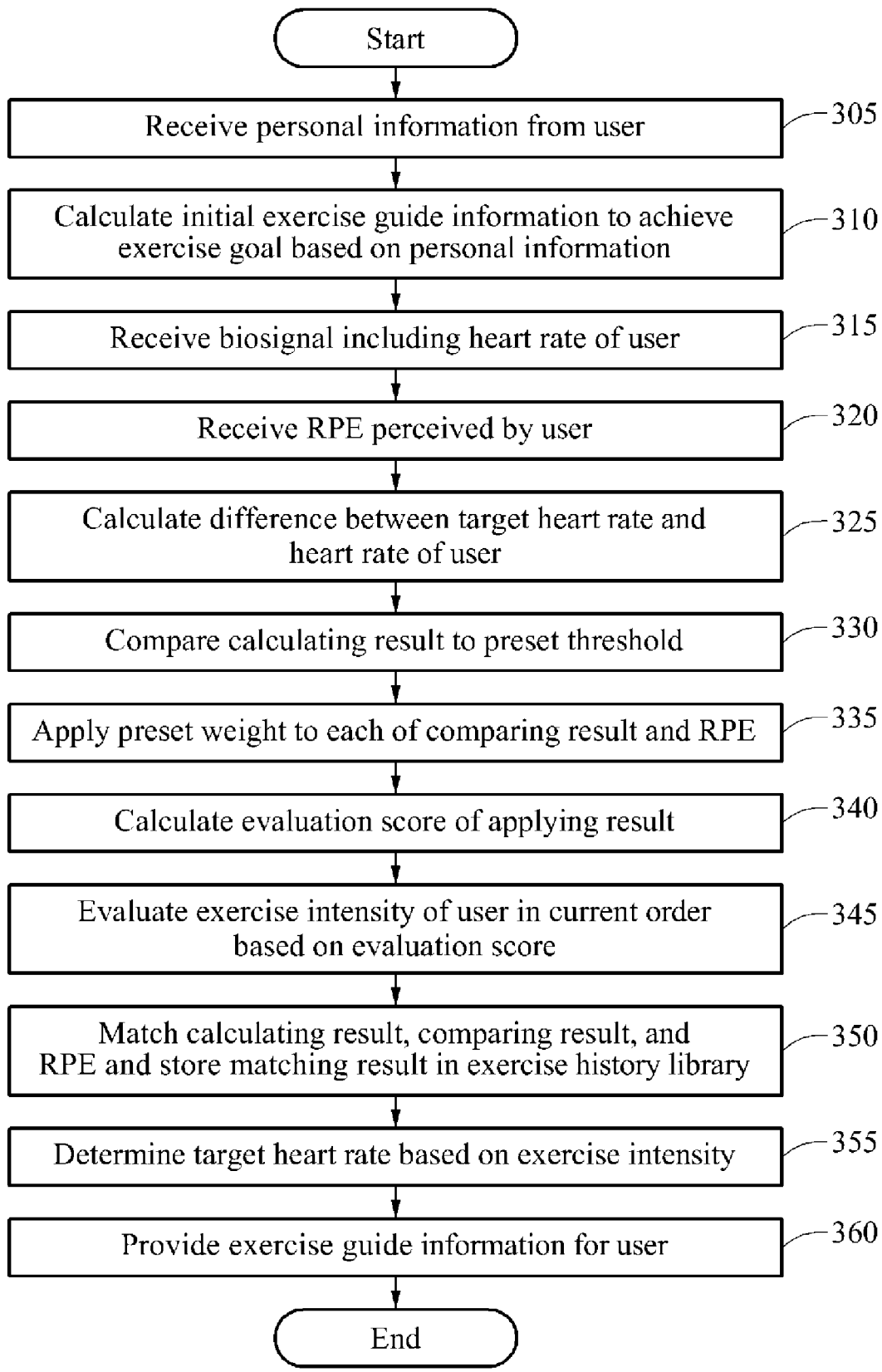
FIG. 3 is a flowchart illustrating an example of a method providing exercise guide information, according to one or more embodiments.

FIG. 3 is a flowchart illustrating an example of a method providing exercise guide information, according to one or more embodiments.

Referring to FIG. 3, in operation 305, personal information may be obtained/received, e.g., by the providing apparatus of FIG. 1, from a user. The personal information may include, for example, at least one of an exercise type, an exercise goal, and body information, noting that additional and/or alternative personal information may also be obtained/received.

The exercise type may include, for example, running, jumping rope, physical training (PT) workouts, and CrossFit workouts, as only non-limiting examples. The exercise goal may include, for example, calorie consumption, and weight loss by exercise, as only non-limiting examples. The body information may include, as only examples, any or any combination of a gender, a weight, a height, a measurement of bust, and a measurement of waist of the user.

In operation 310, initial exercise guide information to achieve the exercise goal may be calculated, e.g., by the providing apparatus, based on the personal information input in operation 305. The initial exercise guide information may include at least one of an exercise intensity, a target heart rate, and an exercise duration, for example, to achieve the exercise goal based on the exercise type to be performed by the user.

For example, the providing apparatus may calculate initial exercise guide information by searching for or calculating an exercise intensity, and an exercise duration to be performed by a woman who is 165 centimeters (cm) in height and 60 Kg in weight to achieve an exercise goal of 3-kilogram (Kg) weight loss based on pre-stored statistics or research data.

In operation 315, a biosignal including a heart rate of the user obtained through a wearable device may be received. As only an example, the providing apparatus may receive, obtained through the wearable device, at least one of biosignals of the user sensed before an exercise of a current order, during the exercise of the current order, and/or within a predetermined time period after the exercise of the current order.

In operation 320, an RPE perceived by the user with respect to the exercise of the current order may be received/obtained. As only an example, the providing apparatus may display, on a touch display, potential exercise intensities with respect to the exercise of the current order in a form of a plurality of levels, as shown in FIG. 6, for the user to select a corresponding level, or may enable the user to input the RPE using a voice through a voice guide as shown in FIG. 7. The user may input the RPE perceived by the user by selecting one of the plurality of levels displayed on the touch display.

The providing apparatus may evaluate/determine an exercise intensity of the user in the current order based on the biosignal received in operation 315 and the RPE received in operation 320.

The exercise intensity may be evaluated/determined using the following non-limiting example method.

In operation 325, a difference between a target heart rate and the heart rate of the user, received in operation 315, may be calculated. In this example, the target heart rate may be predetermined based on the initial exercise guide information or user settings, or may be determined based on an exercise intensity evaluated with respect to an exercise of a previous order through iterative exercise performances.

In operation 330, a result of the calculating of operation 325 may be compared to a preset threshold.

In operation 335, a preset weight may be applied to each of a result of the comparing of operation 330 and the RPE received in operation 320. For example, when the result of comparing of operation 330 corresponds to "3", the providing apparatus may multiply "3" by a weight of "1", and multiply the received RPE of "6" by a weight of "2".

In operation 340, an evaluation score may be calculated for the result of the applying of operation 335. For example, the providing apparatus may calculate the evaluation score of the result of applying, as expressed by 3×1+6×2=3+12=15.

In operation 345, the exercise intensity of the user in the current order may be evaluated based on the evaluation score determined in operation 340, for example, the score of "15".

In an example, an evaluation score of the result of comparing of operation 330 or the RPE received in operation 320 may be separately calculated and used to evaluate the exercise intensity of the user.

In operation 350, the result of calculating of operation 325, the result of comparing of operation 330, and the RPE received in operation 320 may be matched, and a result of the matching stored in an exercise history library.

In operation 355, a target heart rate of the user may, thus, be determined based on the exercise intensity evaluated in operation 345. The target heart rate of the user may be for an exercise of a next order of the user.

In operation 360, exercise guide information may be provided to the user based on the exercise intensity evaluated in operation 345. The exercise guide information may be provided by the providing apparatus and may be exercise guide information for the current order or a next or future order.

Figure 4:
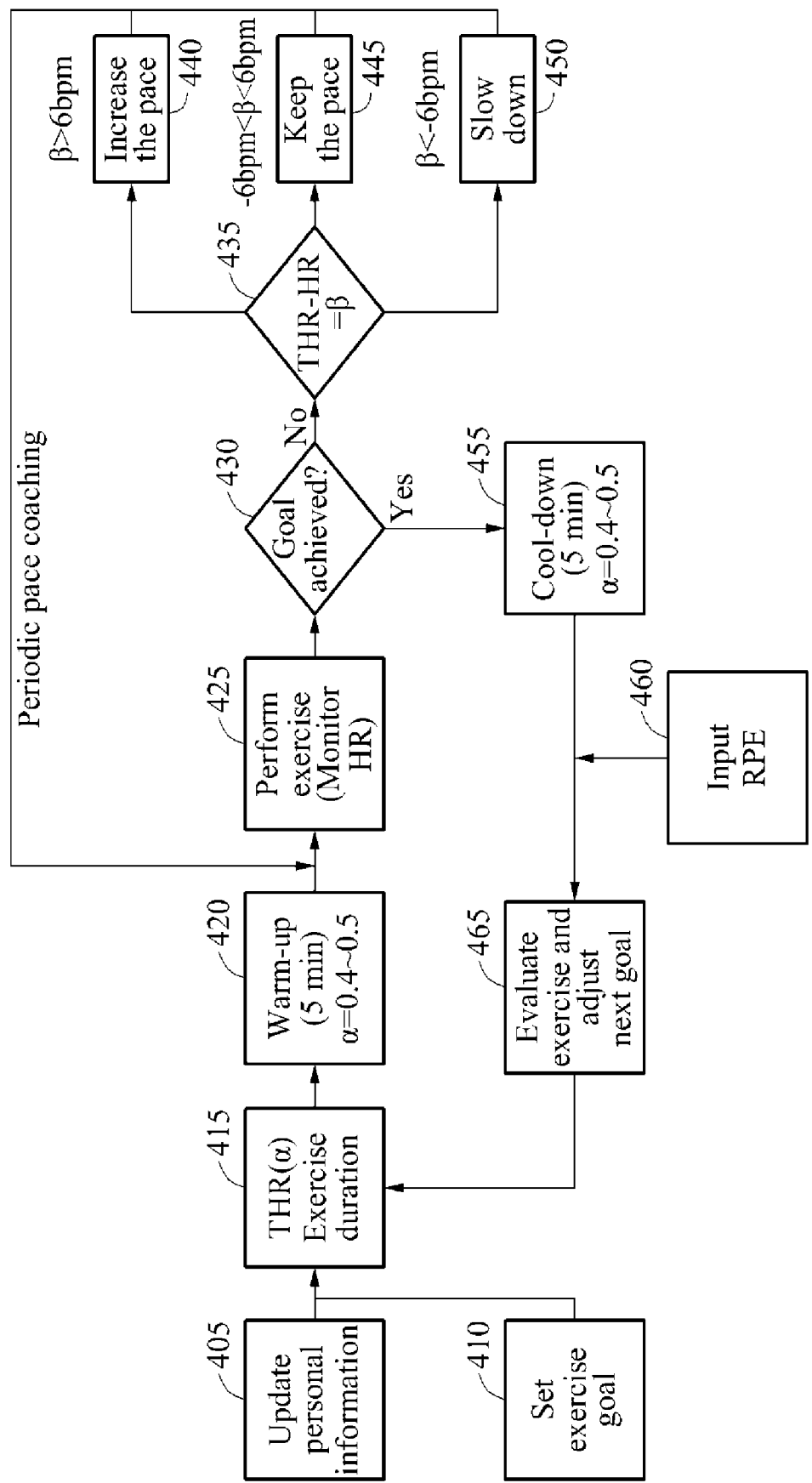
FIG. 4 is a flowchart illustrating an example of a method providing exercise guide information, according to one or more embodiments.

FIG. 4 is a flowchart illustrating an example of a method providing exercise guide information, according to one or more embodiments.

Referring to FIG. 4, in operation 405, personal information or updated personal information may be obtained/received from a user. The personal information may include, for example, an exercise type to be performed by the user and body information.

In operation 410, an exercise goal may be received from the user. In an embodiment, exercise goal may be obtained/received by the providing apparatus of FIG. 1. The exercise goal may include, for example, an exercise duration, an exercise intensity, calorie consumption, and weight loss.

In operation 415, a target heart rate THR of the user or the exercise duration may be determined, e.g., by the providing apparatus, based on the received information, for example, the personal information and the exercise goal.

As only example, and noting that alternatives are available, the target heart rate THR may be determined based on the Karvonen formula, THR=(HRmax−HRrest)×α+HRrest, and an exercise intensity set by the user.

HRmax denotes a maximum heart rate recommended by American College of Sports and Medicine (ACSM) based on an age of a user, and may be obtained by an equation of, for example, HRmax=206.9−0.67×Age.

HRrest denotes a resting heart rate, a heart rate measured when a user maintains a static state before performing an exercise. The variable a denotes a target intensity which is an index of an exercise intensity, and may have a value of 0<α<1 based on an exercise objective of the user.

In operation 420, the user may be guided to perform a warm-up exercise, for example, at the target intensity α of 0.4 to 0.5 for 5 minutes. In an embodiment, the guidance may be provided by the providing apparatus, for example.

When the user performs an exercise after the warm-up exercise, a biosignal including a heart rate of the user received through a wearable device may be monitored during the exercise, e.g., by the providing apparatus, in operation 425.

In operation 430, there may be a determination, e.g., by the providing apparatus, as to whether the user has achieved the exercise goal, for example, the exercise duration, input in operation 410, based on a result of the monitoring of operation 425.

When the exercise goal has been achieved, as a result of the determining of operation 430, the providing apparatus, for example, may guide the user to perform a cool-down exercise, in operation 455. The cool-down exercise may be performed at the same intensity for the same duration as those of the warm-up exercise, for example, at the target intensity α of 0.4 to 0.5 for 5 minutes.

When the cool-down exercise is terminated, an RPE, as perceived by the user through exercise performance, maybe received/obtained using a UI of the providing apparatus, for example, in operation 460.

In operation 465, the exercise intensity of the current order may be evaluated/determined based on a result of the monitoring of operation 425 and the RPE received in operation 460, and an exercise goal for an exercise of a next order may be set or adjusted. For example, the providing apparatus may evaluate the exercise intensity of the user based on the biosignal such as a heart rate or a heartbeat pattern, with respect to the exercise of the current order, and the RPE perceived by the user, and establish the exercise goal for the next order.

The providing apparatus may use the exercise goal, for example, a target heart rate, set or adjusted in operation 465 as the target heart rate of operation 415 for the exercise of the next order.

When the exercise goal is yet to be achieved, e.g., according to the determining of operation 430, a difference between the target heart rate THR and the heart rate HR of the user, sensed during the monitoring of operation 425, may be calculated, as expressed by THR−HR=β. The calculated β may be compared to a preset threshold, for example, 6 beats per minute (bpm), in operation 435. The providing apparatus, for example, may then determine whether the current exercise intensity is excessive, moderate, or low in comparison to the target heart rate THR of the user based on a result of this comparison.

When the heart rate HR of the user at the current exercise intensity is determined to be low in comparison to the target heart rate THR of the user, as a result of the comparing of operation 435, for example, β>6 bpm, the providing apparatus may provide exercise guide information to the user to increase the current exercise intensity, for example, increase the pace, in operation 440.

When the heart rate HR of the user at the current exercise intensity is determined to be moderate in comparison to a history of the target heart rate THR of the user, as a result of the comparing of operation 435, for example, −6 bpm<β<6 bpm, the providing apparatus may provide exercise guide information to maintain the current exercise intensity, for example, keep the pace, in operation 445.

When the heart rate HR of the user at the current exercise intensity is determined to be high in comparison to a history of the target heart rate THR of the user, as a result of the comparing of operation 435, for example, β<−6 bpm, the providing apparatus may provide exercise guide information to decrease the current exercise intensity, for example, slow down, in operation 450. In this example, when the exercise intensity is determined to be excessively higher than a predetermined threshold, the providing apparatus may provide a warning message to the user. Further, when arrhythmia is sensed in the heartbeat pattern of the user, the providing apparatus may inform a pre-designated person or hospital of the sensing of arrhythmia.

In operation 425, the biosignal of the user with respect to exercise performance may be re-monitored, or continued to be monitored, e.g., by the providing apparatus, after the exercise guide information is provided.

Figure 5:
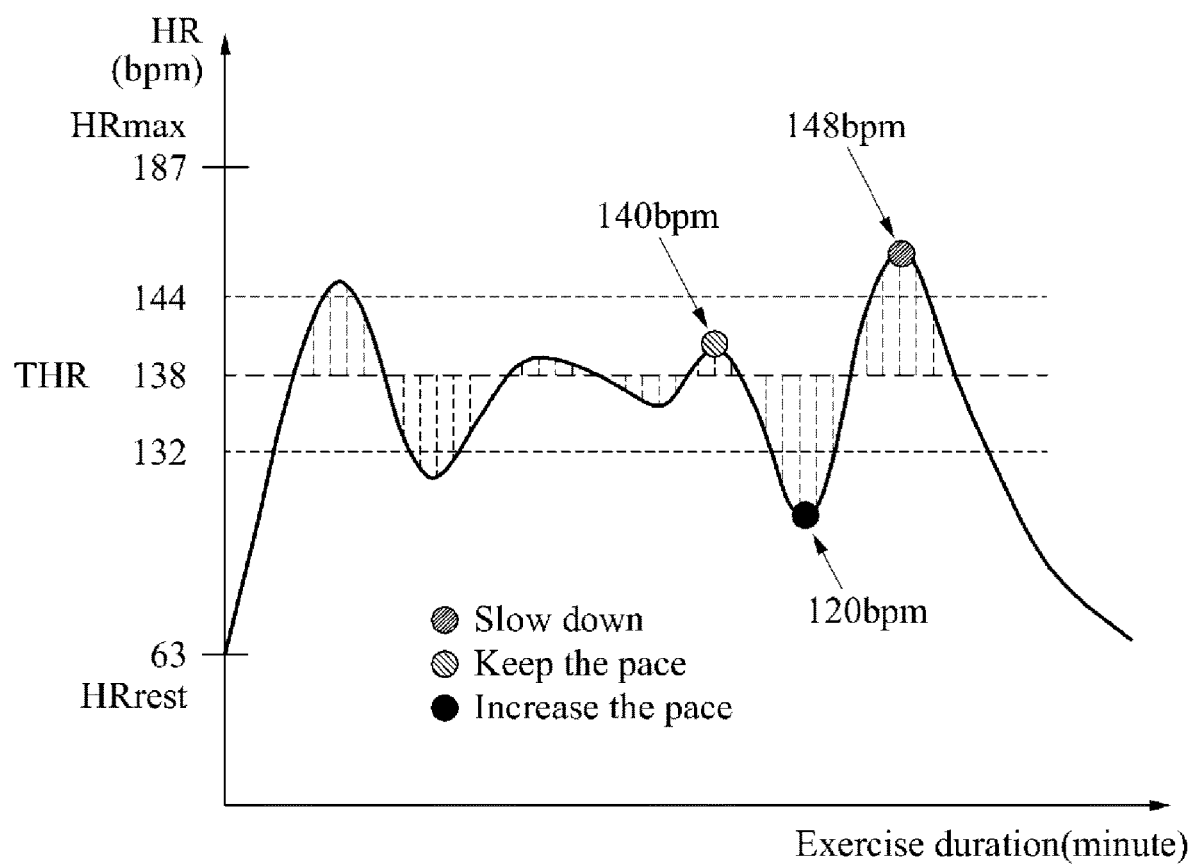
FIG. 5 is a graph illustrating an example of a method evaluating an exercise intensity of a user, according to one or more embodiments.

FIG. 5 is a graph illustrating an example of a method evaluating an exercise intensity of a user, according to one or more embodiments.

Referring to FIG. 5, the graph shows a change in a heart rate HR of a user based on a target heart rate THR with respect to a change in an exercise duration, and exercise guide information provided based on the change in the heart rate of the user.

For example, it may be assumed that a user is 30 years old, an HRrest of the user measured when the user maintains a static state before an exercise is initiated is 63 bpm, a target exercise intensity α desired by the user is 0.6, and a heart rate threshold T is 6 bpm.

In this example, a maximum heart rate HRMax of the user may be obtained as expressed by HRmax=206.9−(0.67× Age)=206.9−(0.67×30)=206.9−20.1=186.8.

The target heart rate THR may be obtained by the Karvonen Formula and the target intensity α desired or set by the user, as expressed by:
THR=(HRmax−HRrest)×α+HRrest=(186.8−63)×0.6+ 63=74.28+63=137.28. The obtained target heart rate THR may be rounded up to 138 bpm.

When the target heart rate THR is 138 bpm and the heart rate HR of the user is 140 bpm, −6 bpm<(THR−HR=138 bpm−140 bpm=−2 bpm)<6 bpm may be satisfied. Thus, a providing apparatus may evaluate/determine the current exercise intensity to be moderate. The providing apparatus may provide exercise guide information to maintain the current exercise intensity.

When the heart rate HR of the user is 148 bpm, (THR−HR=138 bpm−148 bpm)=−10 bpm<−6 bpm may be satisfied. Thus, the providing apparatus may determine the current exercise intensity is strong. The providing apparatus may provide exercise guide information to the user to decrease the current exercise intensity.

When the heart rate HR of the user is 120 bpm, (THR−HR=138 bpm−120 bpm=10 bpm>6 bpm may be satisfied. Thus, the providing apparatus may determine the current exercise intensity is weak. The providing apparatus may provide exercise guide information to the user to increase the current exercise intensity.

FIG. 6 illustrates an example of a screenshot of a touch display configured to receive an RPE perceived by a user, according to one or more embodiments.

Referring to FIG. 6, a plurality of levels indicating potential exercise intensities of a current order to receive an RPE perceived by a user is illustrated.

The potential exercise intensities may be displayed as, for example, 10 levels. When a first level is an exercise intensity corresponding to a rest, a higher level may indicate a higher exercise intensity perceived by a user. A tenth level may be a highest exercise intensity requiring a maximum exertion.

For example, a fifth level may be a moderate exercise intensity for the user. In this example, when an RPE input by the user is higher than or equal to a sixth level, a providing apparatus may decrease a target heart rate.

When the RPE input by the user is higher than or equal to a fourth level and lower than or equal to the sixth level, the providing apparatus may maintain the target heart rate to be equal to a current set value. When the RPE input by the user is lower than or equal to the fourth level, the providing apparatus may increase the target heart rate.

FIG. 7 is a diagram illustrating an example of receiving an RPE perceived by a user using a voice, according to one or more embodiments.

Referring to FIG. 7, an example of receiving an RPE perceived by a user through a microphone connected to a UI is illustrated.

A mobile device 700 includes a memory 710, a processor 720, a guide provider 730, a speaker 735, a UI 740, and a microphone 745, for example. The descriptions of the operations of the memory 151, the processor 153, the UI 155, and the guide provider 157 of FIG. 1 may be applicable to the memory 710, the processor 720, the UI 740, and the guide provider 730 and thus, duplicated descriptions will be omitted for conciseness.

The speaker 735 may provide an audio guide provided by the guide provider 735 to receive/obtain an RPE of the user. The audio guide to receive the RPE may include contents, for example, "How do you like the current exercise intensity?", or "Please select the current exercise intensity from level 1 to 10. Level 10 is the maximum intensity."

The user may answer to the audio guide provided through the speaker 735, for example, "Very light", "Very hard", "Moderate", "Level 1", or "Level 5". The answer of the user may be transmitted to the processor 720 through the microphone 745 and the UI 740 as the RPE perceived by the user.

Figure 8:
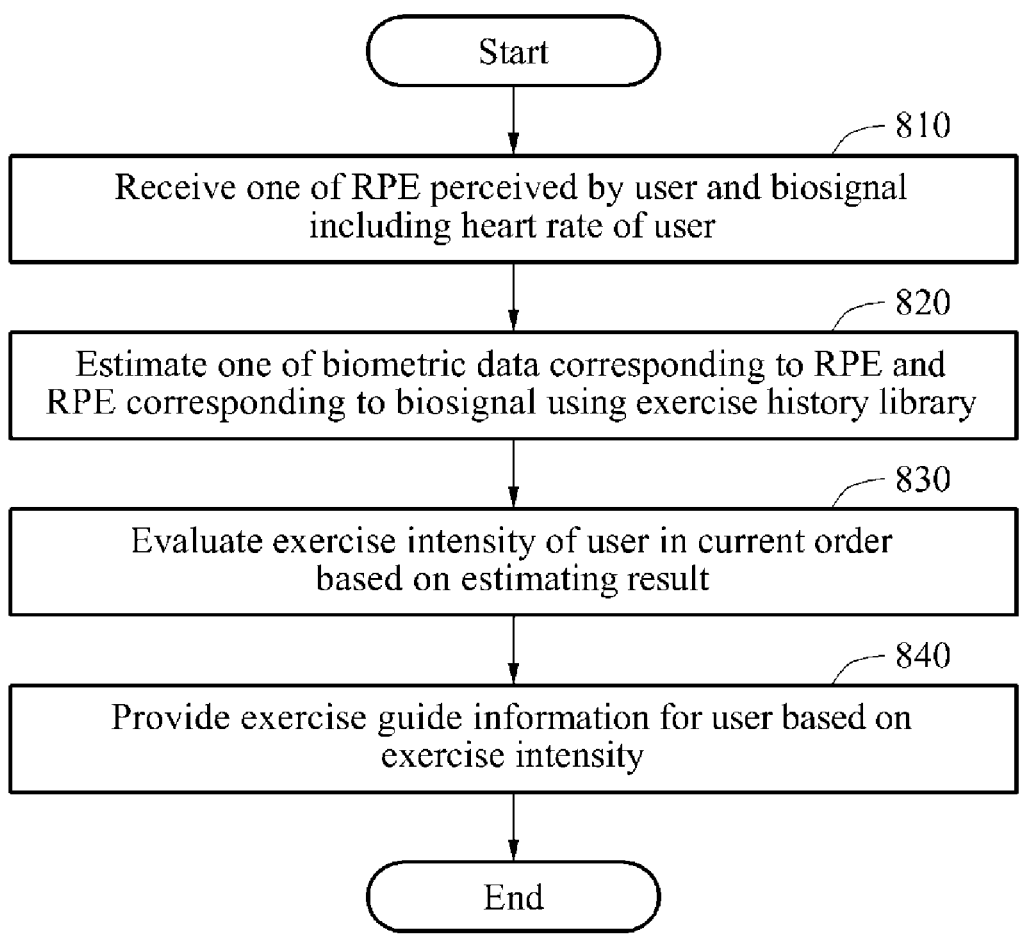
FIG. 8 is a flowchart illustrating an example of a method providing exercise guide information, according to one or more embodiments.

FIG. 8 is a flowchart illustrating an example of a method providing exercise guide information, according to one or more embodiments.

Referring to FIG. 8, an example of providing exercise guide information through mutual estimation, in a case in which information on one of a measured heart rate and an RPE perceived by a user is provided, is illustrated.

In operation 810, one of an RPE perceived by a user with respect to an exercise of a current order and a biosignal including a heart rate of the user may be received. For example, the providing apparatus of FIG. 1 may receive or obtain only one, or only one may be available, of the RPE and the biosignal including the heart rate of the user.

In operation 820, one of biometric data corresponding to the received RPE and an RPE corresponding to the received biosignal may be estimated, e.g., by the providing apparatus, using an exercise history library containing cumulative information associated with an exercise of a previous order. When a heart rate is yet to be measured by a wearable device, the providing apparatus may estimate a heart rate or a heartbeat pattern based on an RPE stored in the exercise history library using a linear regression method or a neural network such as an artificial neural network (ANN), for example.

Here, the biosignal may be, for example, a cumulative calculation result $$\varepsilon = \sum_{1}^{n} (HR - THR)$$

of a difference between a target heart rate THR and a sensed heart rate HR of the user, or average heart rate information ε/n.

The providing apparatus may distinguish criteria for a high-intensity exercise, a mid-intensity exercise, and a low-intensity exercise based on an RPE input by a user, in providing exercise guide information.

The RPE may be a subjective value input by a user. However, when statistics are accumulated, the RPE may have a tendency of being proportional to an exercise intensity. The RPE and the heart rate HR may have a relationship as expressed by, for example, RPE=0.72+0.081×HR.

When one of the heart rate of the user and the RPE is available, e.g., only one of the heart rate and RPE, the providing apparatus may estimate a value of the other according to statistics using the above equation.

The providing apparatus may classify an exercise intensity based on the RPE and provide exercise guide information, thereby providing an objective basis for the user to safely and progressively perform an exercise within a predetermined heart rate range.

In operation 830, an exercise intensity of the user in the current order may be evaluated/determined, e.g., by the providing apparatus, based on a result of the estimating of operation 820.

In operation 840, exercise guide information may be provided to the user based on the exercise intensity evaluated in operation 830. For example, the providing apparatus may provide the exercise guide information to the user.

Figure 9:
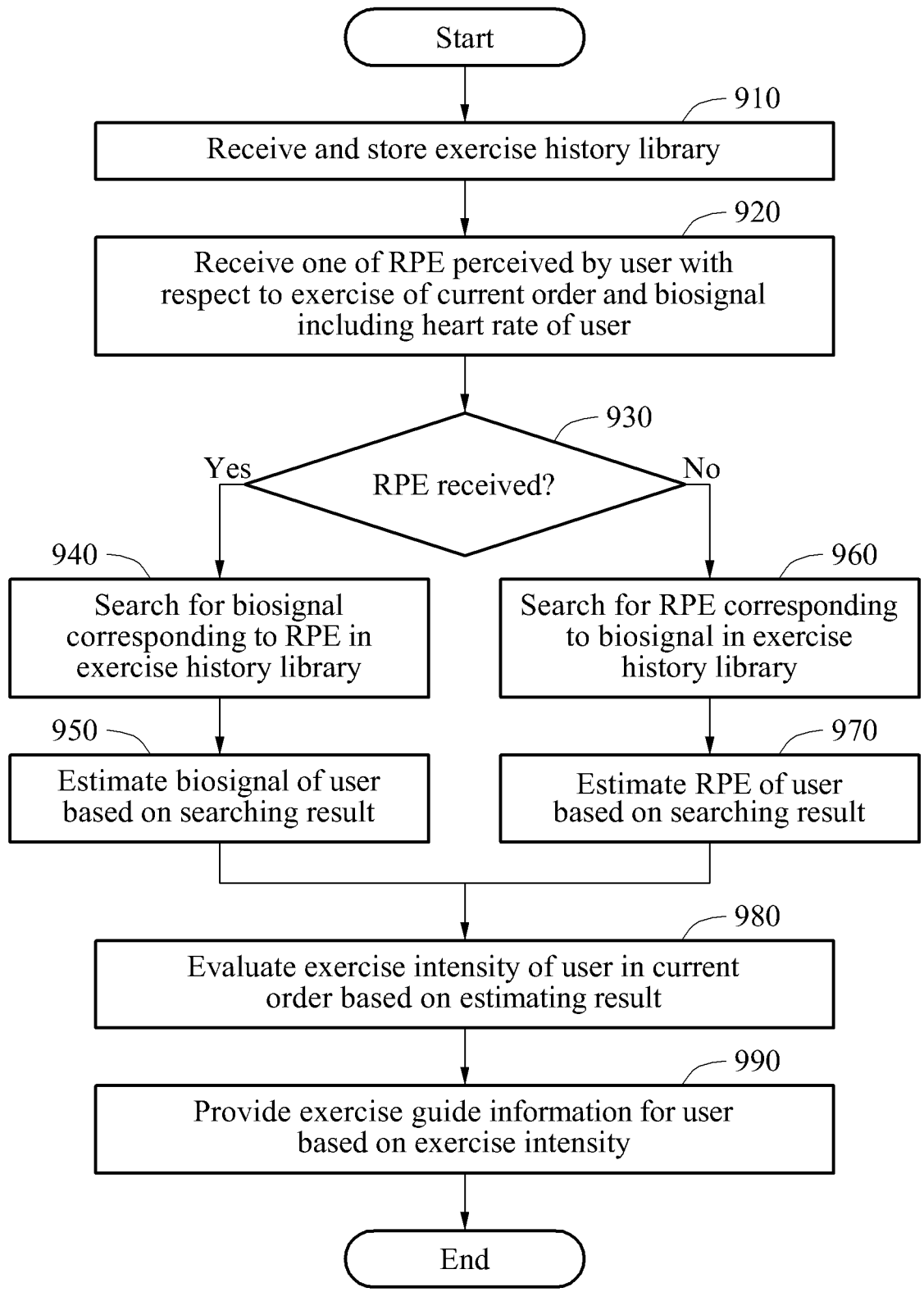
FIG. 9 is a flowchart illustrating an example of a method providing exercise guide information, according to one or more embodiments.

FIG. 9 is a flowchart illustrating an example of a method providing exercise guide information, according to one or more embodiments.

Referring to FIG. 9, in operation 910, a providing apparatus may receive and store, or already include/maintain, an exercise history library containing cumulative information associated with an exercise of a previous order.

The exercise history library may contain at least one of exercise records for exercises of previous orders, average heart rate information including an average cumulative value of differences between target heart rates in the exercises of the previous orders and the respective heart rate of the user, a result of comparing such average heart rate information to a preset threshold, and a respective RPE of the user corresponding to the result of comparing.

In operation 920 one of an RPE perceived by a user with respect to an exercise of a current order and a biosignal including a heart rate of the user may be received. For example, the providing apparatus of FIG. 1 may receive or obtain only one, or only one may be available, of the RPE and the biosignal including the heart rate of the user.

In operation 930, the providing apparatus, for example, may determine whether an RPE is received in operation 920.

As a result of the determining of operation 930, when an RPE is determined to have been received, the example providing apparatus may search for a biosignal corresponding to the received RPE in the exercise history library in operation 940. In this example, the biosignal may be, for example, average heart rate information, e.g., a stored average heart rate information that has been matched, or sufficiently matched, to the received RPE.

In operation 950, the providing apparatus estimates a biosignal of the user in the current order based on a result of the searching of operation 940.

As a result of the determining of operation 930, when an RPE is not received, that is, when a biosignal is received, the example providing apparatus may search for an RPE corresponding to the biosignal in the exercise history library in operation 960, e.g., a stored RPE that has been matched, or sufficiently matched, to the received biosignal.

In operation 970, the example providing apparatus may estimate an RPE of the user in the current order based on a result of the searching of operation 960.

In operation 980, an exercise intensity of the user in the current order may be evaluated/determined based on a result of the estimating of operation 950 or 970. For example, the providing apparatus may evaluate/determine the exercise intensity.

In operation 990, exercise guide information may be provided to the user, e.g., by the providing apparatus, based on the exercise intensity evaluated in operation 980.

Figure 10:
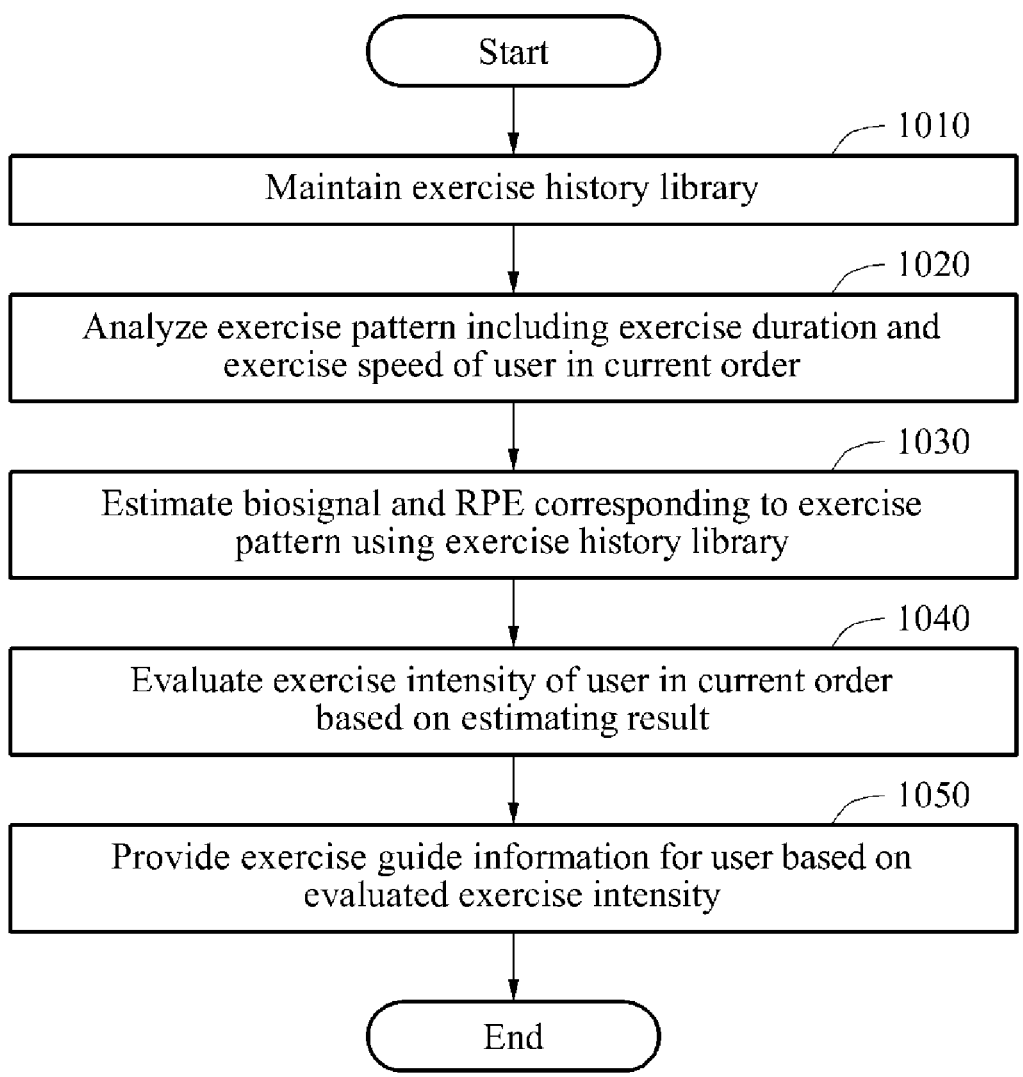
FIG. 10 is a flowchart illustrating an example of a method providing exercise guide information, according to one or more embodiments.

FIG. 10 is a flowchart illustrating an example of a method providing exercise guide information, according to one or more embodiments.

Referring to FIG. 10, FIG. 10 demonstrates an example of providing exercise guide information by estimating both a biosignal, for example, average heart rate information, and an RPE, based on an exercise pattern including a measurement result, for example, an exercise speed, of an accelerometer, and a total exercise duration, e.g., in a case in which neither a heart rate measured by a wearable device nor an RPE perceived by a user is available.

In operation 1010, an exercise history library containing cumulative information associated with an exercise of a previous order may be available or maintained. For example, the exercise history library may be stored or maintained by the providing apparatus of FIG. 1.

In operation 1020, an exercise pattern including an exercise duration and an exercise speed of a user in the current order may be analyzed, e.g., by the providing apparatus.

In operation 1030, a biosignal and an RPE corresponding to the exercise pattern may both be estimated using the exercise history library. For example, the providing apparatus may search for at least one of a biosignal and an RPE corresponding to the exercise pattern in the exercise history library, and estimate a biosignal and an RPE, e.g., for the current order, based on a result of the searching.

In operation 1040, an exercise intensity of the user in the current order may be evaluated/determined, e.g., by the providing apparatus, based on a result of the estimating of operation 1030. In operation 1050, the providing apparatus, for example, provides exercise guide information to the user based on the evaluated exercise intensity.

For example, a user may run at a speed of 10 kilometers per hour (Km/h) for 15 minutes and walk at a speed of 3 Km/h for 20 minutes on a treadmill or outdoors. The providing apparatus may analyze an exercise pattern of the user, for example, an exercise duration and an exercise speed performed by the user, and search for a historical exercise record, in the exercise history library, that corresponds to running at a speed of 10 Km/h for 15 minutes and walking at a speed of 3 Km/h for 20 minutes.

In this example, when an exercise record having at least a predetermined similarity, for example, an exercise record of running at a speed of 10 Km/h for 10 minutes and walking at a speed of 3 Km/h for 10 minutes, is present in the exercise history library, e.g., although an exercise record completely matching with the exercise pattern of the user is absent in the exercise history library, the exercise record having at least a predetermined similarity may be found by the providing apparatus.

The providing apparatus may estimate or use the found biosignal and RPE, corresponding to the found exercise record, as the biosignal and RPE for the current exercise pattern of the user.

The providing apparatus may then evaluate an exercise intensity of the user in the current order based on the estimated biosignal and the estimated RPE, and provide exercise guide information for the user.

Figure 11:
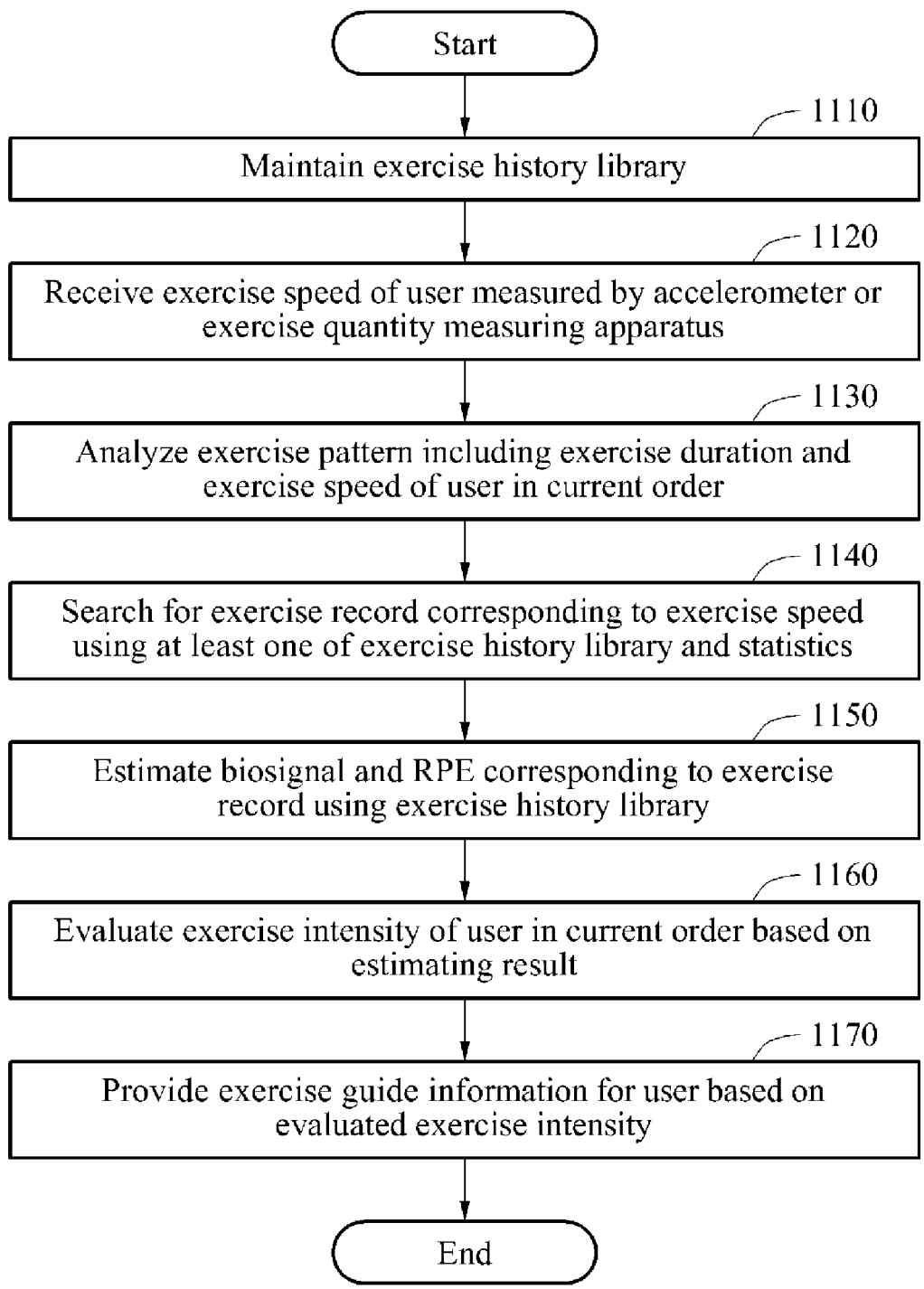
FIG. 11 is a flowchart illustrating an example of a method providing exercise guide information, according to one or more embodiments.

FIG. 11 is a flowchart illustrating an example of a method providing exercise guide information, according to one or more embodiments.

Referring to FIG. 11, in operation 1110, an exercise history library containing cumulative information associated with an exercise of a previous order may be maintained, e.g., by the providing apparatus of FIG. 1.

In operation 1120, an exercise speed of a user measured by an accelerometer or an exercise quantity measuring apparatus may be received by the providing apparatus, for example.

In operation 1130, an exercise pattern including the exercise speed received in operation 1120 and an exercise duration of the user in a current order may be analyzed by the example providing apparatus.

In operation 1140, an exercise record corresponding to the exercise speed may be searched for using at least one of the exercise history library and statistics.

In operation 1150, a biosignal and an RPE corresponding to the exercise record may be estimated by the example providing apparatus using the exercise history library.

In operation 1160, an exercise intensity of the user in the current order may be evaluated/determined by the example providing apparatus based on a result of the estimating of operation 1150. In operation 1170, the exercise guide information may be provided to the user based on the evaluated exercise intensity. For example, the providing apparatus may provide the exercise guide information based on the evaluated exercise intensity.

Figure 12:
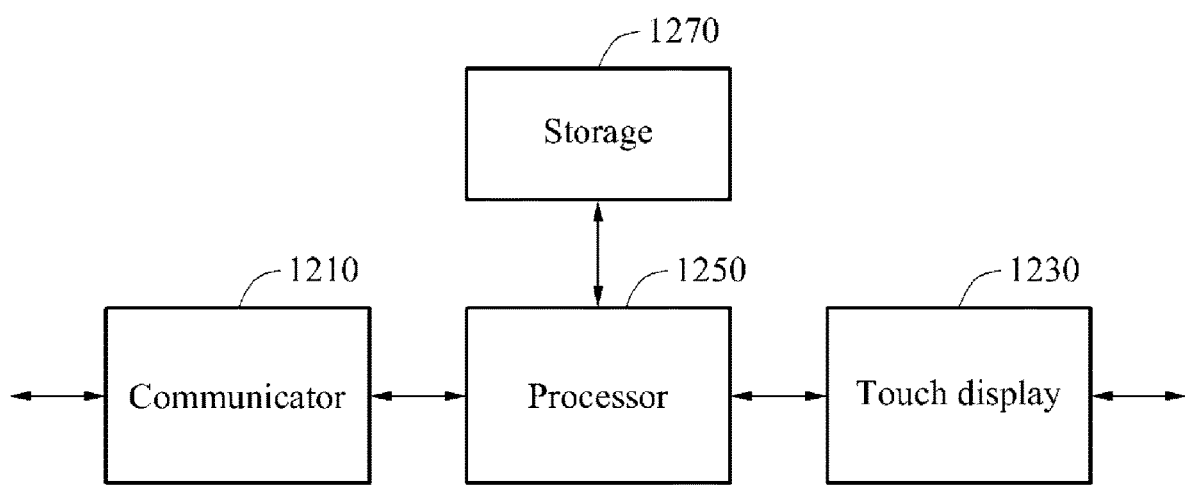
FIG. 12 is a block diagram illustrating an example of an apparatus configured to provide exercise guide information, according to one or more embodiments.

FIG. 12 is a block diagram illustrating an example of an apparatus configured to provide exercise guide information, according to one or more embodiments.

Referring to FIG. 12, a providing apparatus 1200 includes a communicator 1210, a touch display 1230, a processor 1250, and a storage 1270, for example.

The communicator 1210 may receive a biosignal including a heart rate of a user through a wearable device.

The touch display 1230 may display potential exercise intensities with respect to an exercise of a current order as a plurality of levels, and receive an input by the user for a level corresponding to an RPE perceived by the user, among the plurality of levels.

The processor 1250 may evaluate/determine an exercise intensity of the user in the current order based on the biosignal received through the communicator 1210 and the RPE received through the touch display 1230. The processor 1250 may provide exercise guide information for the user with respect to the current order or a next or future order based on the evaluated exercise intensity.

The processor 1250 may calculate a difference between a target heart rate and the heart rate of the user, and compare a result of the calculating to a preset threshold. The processor 1250 may evaluate the exercise intensity of the user in the current order based on a result of the comparing and the RPE received through the touch display 1230.

The storage 1270 may store an exercise history library in which the result of comparing performed by the processor 1250 and the RPE received through the touch display 1230 are matched and stored. The exercise history library may contain cumulative information associated with an exercise of a previous order.

The exercise history library may be stored in the storage 1270, for example, in a form of a database.

Figure 13:
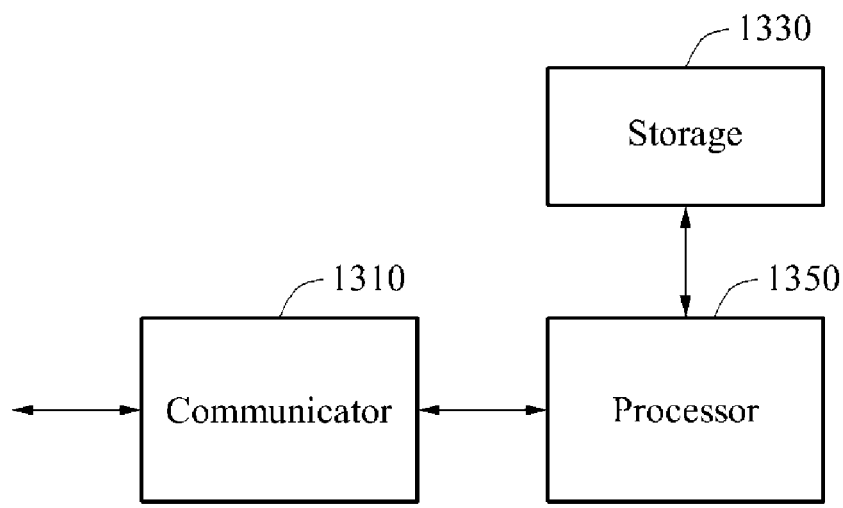
FIG. 13 is a block diagram illustrating an example of an apparatus configured to provide exercise guide information, according to one or more embodiments.

FIG. 13 is a block diagram illustrating an example of an apparatus configured to provide exercise guide information, according to one or more embodiments.

Referring to FIG. 13, a providing apparatus 1300 includes a communicator 1310, a storage 1330, and a processor 1350, for example.

The communicator 1310 may receive one of an RPE perceived by a user with respect to an exercise of a current order and a biosignal including a heart rate of the user. For example, the providing apparatus may receive or obtain only one, or only one may be available, of the RPE and the biosignal including the heart rate of the user.

The storage 1330 may store an exercise history library containing cumulative information associated with an exercise of a previous order.

The exercise history library may contain at least one of exercise records for exercises of previous orders, average heart rate information including an average cumulative value of differences between target heart rates in the exercises of the previous orders and the respective heart rate of the user, a result of comparing such average heart rate information to a preset threshold, and respective RPE of the user corresponding to the result of comparing.

The processor 1350 may estimate one of biometric data corresponding to the received RPE and an RPE corresponding to the received biosignal using the exercise history library. The processor 1350 may evaluate/determine an exercise intensity of the user in the current order based on a result of the estimating. The processor 1350 may provide exercise guide information to the user based on the evaluated exercise intensity.

When the RPE is received, the processor 1350 may estimate a biosignal of the user in the current order based on a biosignal found, with respect to the received RPE, in the exercise history library. When the biosignal is received, the processor 1350 may estimate an RPE of the user in the current order based on an RPE found, with respect to the received biosignal, in the exercise history library.

Figure 14:
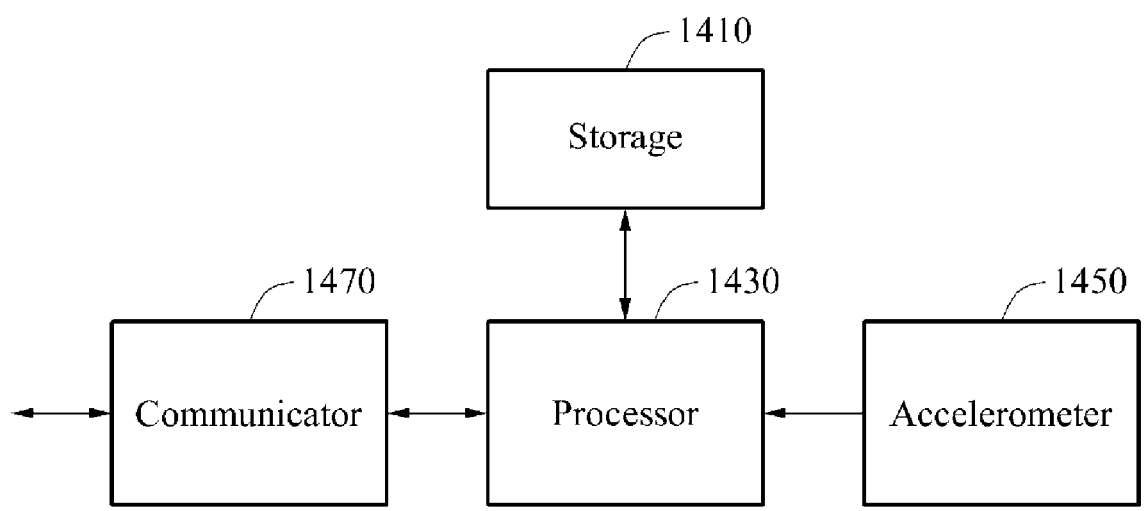
FIG. 14 is a block diagram illustrating an example of an apparatus configured to provide exercise guide information, according to one or more embodiments.

FIG. 14 is a block diagram illustrating an example of an apparatus configured to provide exercise guide information, according to one or more embodiments.

Referring to FIG. 14, a providing apparatus 1400 includes a storage 1410, a processor 1430, an accelerometer 1450, and a communicator 1470, for example.

The storage 1410 may store an exercise history library containing cumulative information associated with an exercise of a previous order.

The processor 1430 may analyze an exercise pattern including an exercise duration and an exercise speed of a user in a current order. The processor 1430 may evaluate/determine an exercise intensity of the user in the current order based on an estimated biosignal and RPE, with respect to the exercise pattern, using the exercise history library. The processor 1430 may provide exercise guide information for the user based on the evaluated exercise intensity.

The processor 1430 may search for at least one of a biosignal and an RPE corresponding to the exercise pattern in the exercise history library, and estimate a biosignal and an RPE, e.g., for the current order, based on a result of the searching.

The accelerometer 1450 may measure the exercise speed of the user.

The communicator 1470 may receive the exercise speed measured by the accelerometer 1450 or an exercise quantity measuring apparatus.

The processor 1430 may search for an exercise record corresponding to the exercise speed using at least one of the exercise history library and statistics, and estimate a biosignal and an RPE corresponding to the exercise record using the exercise history library.

The apparatuses, units, devices, and other components illustrated in FIGS. 1, 6, 7, and 12-14, for example, that may perform one or more operations described herein with respect to any of FIGS. 2-6 and 8-11, for example, are implemented by hardware components. Examples of hardware components include resistors, capacitors, inductors, power supplies, frequency generators, operational amplifiers, power amplifiers, low-pass filters, high-pass filters, band-pass filters, analog-to-digital converters, digital-to-analog converters controllers, sensors, memory, drivers, and any other electronic components known to one of ordinary skill in the art. In one example, the hardware components are implemented by one or more processing devices, or processors, or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer and that may control the processor or computer to implement one or more methods described herein. Hardware components implemented by a processor or computer execute instructions or software, such as an operating system (OS) and one or more software applications that run on the OS, to perform the operations described herein with respect to FIGS. 2-6 and 8-11, for example. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, remote processing environments, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 2-6 and 8-11, for example, that perform the operations described herein may be performed by a processor or a computer as described above executing instructions or software to perform the operations described herein.

Instructions or software to control a processor or computer to implement the hardware components and perform the methods as described above may be written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Based on the disclosure herein, and after an understanding of the same, programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components, such as discussed in any of FIGS. 1, 6, 7, and 12-14, for example, and perform the methods as described above in any of FIGS. 2-6 and 8-11, for example, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

As only an example, a processing device configured to implement a software or computer readable code component to perform an operation A may include a processor programmed to run software or execute computer readable code or instructions to control the processor to perform operation A. In addition, a processing device configured to implement a software or computer readable code component to perform an operation A, an operation B, and an operation C may have various configurations, such as, for example, a processor configured to implement a software or computer readable code component to perform operations A, B, and C; a first processor configured to implement a software or computer readable code component to perform operation A, and a second processor configured to implement a software or computer readable code component to perform operations B and C; a first processor configured to implement a software or compute readable code component to perform operations A and B, and a second processor configured to implement a software or computer readable code component to perform operation C; a first processor configured to implement a software or computer readable code component to perform operation A, a second processor configured to implement a software or computer readable code component to perform operation B, and a third processor configured to implement a software or computer readable code component to perform operation C; a first processor configured to implement a software or computer readable code component to perform operations A, B, and C, and a second processor configured to implement a software or computer readable code component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

As a non-exhaustive example only, an apparatus or system as described herein may be a mobile device, such as a cellular phone, a smart phone, a wearable smart device (such as a ring, a watch, a pair of glasses, a bracelet, an ankle bracelet, a belt, a necklace, an earring, a headband, a helmet, or a device embedded in clothing), a portable personal computer (PC) (such as a laptop, a notebook, a subnotebook, a netbook, or an ultra-mobile PC (UMPC), a tablet PC (tablet), a phablet, a personal digital assistant (PDA), a digital camera, a portable game console, an MP3 player, a portable/personal multimedia player (PMP), a handheld e-book, a global positioning system (GPS) navigation device, or a sensor, or a stationary device, such as a desktop PC, a high-definition television (HDTV), a DVD player, a Blu-ray player, a set-top box, or a home appliance, or any other mobile or stationary device capable of wireless or network communication. In one example, a wearable device is a device that is designed to be mountable directly on the body of the user, such as a pair of glasses or a bracelet. In another example, a wearable device is any device that is mounted on the body of the user using an attaching device, such as a smart phone or a tablet attached to the arm of a user using an armband, or hung around the neck of the user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is not limited by the detailed description, but further supported by the claims and their equivalents, and all variations within the scope of the claims and their equivalents are to be construed as being included in the disclosure.

What is claimed is:

1. A processor-implemented method providing exercise guide information, the method comprising:
   receiving a biosignal that includes a heart rate of a user obtained through a wearable device;
   receiving a rate of perceived exertion (RPE), as indicated by the user, with respect to an exercise of a current order; and
   using one or more processors to:
      adjust, based on respective predetermined variables, either one or both of the received RPE and a result of a threshold consideration by the one or more processors of a difference between the heart rate of the user and a target heart rate;
      determine an exercise intensity of the user in the current order based on an evaluation score determined based on both of the adjusted RPE and the adjusted result of the threshold consideration, based on both of the adjusted received RPE and the result of the threshold consideration, or based on both of the received RPE and the adjusted result of the threshold consideration; and
      control generation of vibrational feedback to the user based on the determined exercise intensity of the user in the current order,
      wherein the controlled generation of the vibrational feedback includes a control of a provision of a first vibration based on a determination, by the one or more processors and dependent on the determined exercise intensity, to provide exercise guidance to increase a movement of the user, and a control of a provision of a second vibration based on a determination, by the one or more processors and dependent on the determined exercise intensity, to provide exercise guidance to decrease the movement of the user.

2. The method of claim 1, wherein the receiving of the biosignal comprises wirelessly receiving, from the wearable device, at least one of biosignals of the user sensed before the exercise of the current order, biosignals of the user sensed during the exercise of the current order, and biosignals of the user sensed within a predetermined time period after the exercise of the current order.

3. The method of claim 1, further comprising:
   calculating initial exercise guide information to achieve an exercise goal based on received personal information.

4. The method of claim 3, further comprising receiving the personal information from the user, the personal information including at least one of an exercise type, the exercise goal, and body information of the user.

5. The method of claim 3, wherein the calculated initial exercise guide information comprises at least one of an initial exercise intensity, the target heart rate, and an exercise duration to achieve the exercise goal based on a user indicated exercise type.

6. The method of claim 1, wherein the receiving of the biosignal, the receiving of the RPE, and provision of the vibrational feedback are performed by the wearable device, where the wearable device includes the one or more processors.

7. The method of claim 1, further comprising:
   calculating the difference between the heart rate of the user and the target rate; and
   matching the calculated difference, the result of the threshold consideration, and the received RPE, and storing a result of the matching in an exercise history library.

8. The method of claim 1, wherein the adjusting, based on the respective predetermined variables, of the either one or both of the received RPE and the result of the threshold consideration comprises:
   applying a first preset weight, as one of the predetermined variables, to the result of the threshold consideration;
   applying a second preset weight, as an other one of the predetermined variables, to the received RPE; and
   calculating the evaluation score as a score of a result of a combining of a result of the applying of the first preset weight and a result of the applying of the second preset weight.

9. The method of claim 1, further comprising:
   determining the target heart rate based on a previous exercise intensity of the user for a previous order; and
   determining a target heart rate for an exercise of a next order of the user based on the determined exercise intensity of the user in the current order.

10. The method of claim 1, further comprising providing the exercise guide information to the user by providing the exercise guide information for next order based on the determined exercise intensity.

11. A non-transitory computer-readable storage medium comprising computer readable code to cause the one or more processors to perform the method of claim 1.

12. The method of claim 1, wherein the provision of the exercise guidance to increase the movement of the user includes a provision of exercise guidance to increase a movement pace of the user, and the provision of the exercise guidance to decrease the movement of the user includes a provision of exercise guidance to decrease a movement pace of the user.

13. A processor-implemented method providing exercise guide information, the method comprising:
iteratively, using one or more processors, generate an exercise history library, with respect to each of a plurality of previous order exercises performed by a user, to match information for a corresponding RPE and biometric information of previous order exercises that are obtained in corresponding generated exercise intensity information of the user in the previous order exercises by the one or more processors, and to represent a proportionality between perceived exertions and exercise intensity over time;
request and detect, using the one or more processors, receipt of a rate of perceived exertion (RPE), as indicated by the user, with respect to an exercise of a current order or receive a biosignal, detected by a wearable device, that includes a heart rate of the user with respect to the exercise of the current order, where the wearable device comprises the one or more processors or another device includes the one or more processors and communicates with the wearable device for the receipt of the biosignal;
obtain, by the one or more processors, a trained machine learning model from a memory of the wearable device or the other device;
generating, using the one or more processors, an estimated biometric data corresponding to the received RPE, or an estimated RPE corresponding to the received biosignal, by implementing the trained machine learning model with respect to the generated exercise history library and the received one of the RPE and the biosignal, the trained machine learning model indicating the estimated biometric data or the estimated RPE; and
generate, using the one or more processors, exercise intensity information of the user in the current order, the generating of the exercise intensity information in the current order comprises generating an evaluation score based on the estimated RPE indicated by the machine learning model, the heart rate of the user, and a target heart rate, or generating the evaluation score based on the received RPE, an estimated heart rate of the user of the estimated biometric data indicated by the machine learning model, and the target heart rate, and generating the exercise intensity information in the current order based on the generated evaluation score; and
control, by the one or more processors, provision of generated exercise guide information to the user based on the generated exercise intensity information.

14. The method of claim 13, wherein the exercise history library contains at least one of exercise records of the previous order exercises, average heart rate information comprising an average cumulative value of differences between target heart rates in the previous order exercises and respective heart rate of the user, a result of comparing the average heart rate information to a preset threshold, and respective RPE of the user corresponding to the result of the comparing.

15. The method of claim 13, wherein the generating of the estimated biometric data includes regression based intuits by the trained machine learning model with respect to plural biosignals in the maintained exercise history library and with respect to the received RPE.

16. The method of claim 13, wherein the generating of the estimated RPE includes regression based intuits by the machine learning model with respect to plural RPEs in the maintained exercise history library with respect to the received biosignal.

17. The method of claim 13, wherein the controlled provision of the generated exercise guide information to the user is performed by the wearable device that includes the one or more processors.

18. The method of claim 13, wherein the generating of the evaluation score based on the estimated RPE, the heart rate of the user, and the target heart rate includes selectively weighting the estimated RPE and selectively weighting a result of a comparison between the heart rate of the user and the target heart rate, or the generating of the evaluation score based on the received RPE, the estimated heart rate, and the target heart rate includes selectively weighting the received RPE and selectively weighting a result of a comparison between the estimated heart rate of the user and the target heart rate.

19. The method of claim 13, wherein the controlled provision of the generated exercise guide information to the user includes a controlling of a selective provision of different vibrational guidance outputs to the user to respectively increase movement exertion and decrease movement exertion based on the generated exercise intensity information.

20. A processor-implemented method of providing exercise guide information, the method comprising using one or more processors to:
iteratively generate an exercise history library, with respect to each of a plurality of previous order exercises performed by a user, to match exercise pattern information with corresponding RPE and biometric information of the previous order exercises, the exercise pattern information and the corresponding RPE and biometric information of the previous order exercises being generated by the one or more processors in corresponding generated exercise intensity information of the user respectively during the previous order exercises;
generate exercise pattern information from a detected exercise pattern of a user performing an exercise in a current order, where the exercise pattern information includes a measured exercise duration and measured exercise speed or measured movement of the user in the current order, where the measured exercise speed or measured movement is based on sensor data of a movement sensor measuring movement of the user;
search the exercise history library with respect to the generated exercise pattern, which is absent in the exercise history library, for stored exercise pattern information that matches the generated exercise pattern with at least a predetermined similarity or that is determined similar to the generated exercise pattern;
generate each of an estimated rate of perceived exertion (RPE) and an estimated biosignal based on information extracted from the exercise history library based on results of the search;
generate exercise intensity information of the user in the current order, the generating of the exercise intensity information in the current order comprises generating an evaluation score based on the estimated RPE, an estimated heart rate of the estimated biosignal, and a target heart rate, and generating the exercise intensity information in the current order based on the generated evaluation score;
generate exercise guide information to the user based on the determined exercise intensity; and control provision of the generated exercise guide information to the user,
wherein the controlled provision of the generated exercise guide information includes a selective control of output guidance to the user to change a current movement exertion by the user.

21. The method of claim 20, further comprising:
receiving the exercise speed of the user from an accelerometer.

22. The method of claim 20, wherein the controlled provision of the generated exercise guide information includes a control of a guidance output to change the current movement exertion by the user to a cool-down intensity based on a predetermined reduction weighting of the generated exercise intensity information.

23. The method of claim 20, wherein the controlled provision of the generated exercise guide information includes a control of a guidance output to change the current movement exertion by the user to stop exercising and contact a medical professional with respect to a heart health of the user.

24. The method of claim 20, wherein the selective control of the output guidance to change the current movement exertion by the user includes a control of a selective provision of different vibrational guidance outputs to the user to respectively increase movement exertion and decrease movement exertion based on the generated exercise intensity information.

25. A wearable device, the wearable device comprising:
a biosensor configured to capture a biosignal that includes a heart rate of a user;
a touch display; and
one or more processors configured to:
control the touch display to display potential exercise intensities with respect to an exercise of a current order as a plurality of levels, and recognize receipt of an input to the touch display indicating a level, of the displayed potential exercise intensities, identifying a rate of perceived exertion (RPE) perceived by the user;
adjust, based on respective predetermined variables, either one or both of the identified RPE and a result of a threshold consideration by the one or more processors of a difference between the heart rate of the user and a target heart rate;
determine an exercise intensity of the user in the current order based on an evaluation score determined based on both of the adjusted RPE and the adjusted result of the threshold consideration, based on both of the adjusted identified RPE and the result of the threshold consideration, or based on both of the identified RPE and the adjusted result of the threshold consideration; and
control generation of vibrational feedback by the wearable device to the user with respect to the current order based on the determined exercise intensity,
wherein the control of the generation of the vibrational feedback includes a controlling of the wearable device to provide a first vibration based on a determination, by the one or more processors and dependent on the determined exercise intensity, to provide exercise guidance to increase a movement pace of the user, and a controlling of the wearable device to provide a second vibration based on a determination, by the one or more processors and dependent on the determined exercise intensity, to provide exercise guidance to decrease the movement pace of the user.

26. The apparatus of claim 25, further comprising:
a storage configured to store an exercise history library in which the result of the threshold consideration and the RPE are matched and stored.

27. An apparatus configured to provide exercise guide information, the apparatus comprising:
a storage including an exercise history library; and
one or more processors configured to:
iteratively generate the exercise history library, with respect to each of a plurality of previous order exercises performed by a user, to match information for a corresponding RPE and biometric information of previous order exercises that are obtained in corresponding generated exercise intensity information of the user in the previous order exercises by the one or more processors, and to represent a proportionality between perceived exertions and exercise intensity over time;
request and detect receipt of a rate of perceived exertion (RPE), as indicated by the user, with respect to an exercise of a current order or receive a biosignal, detected by a wearable device, that includes a heart rate of the user with respect to the exercise of the current order, where the wearable device comprises the one or more processors or another device includes the one or more processors and communicates with the wearable device for the receipt of the biosignal;
obtain a trained machine learning model from a memory of the wearable device or the other device;
generate an estimated biometric data corresponding to the received RPE, or an estimated RPE corresponding to the received biosignal, by implementing the trained machine learning model with respect to the generated exercise history library and the received one of the RPE and the biosignal, the trained machine learning model indicating the estimated biometric data or the estimated RPE;
generate exercise intensity information of the user in the current order, the generating of the exercise intensity information in the current order comprises generating an evaluation score based on the estimated RPE indicated by the machine learning model, the heart rate of the user, and a target heart rate, or generating the evaluation score based on the received RPE, an estimated heart rate of the user of the estimated biometric data indicated by the machine learning model, and the target heart rate, and generating the exercise intensity information in the current order based on the generated evaluation score; and
control provision of generated exercise guide information to the user based on the generated exercise intensity information.

28. The apparatus of claim 27, wherein the exercise history library contains at least one of exercise records for the previous order exercises, average heart rate information including an average cumulative value of differences between target heart rates in the previous order exercises and respective heart rate of the user, a result of comparing the average heart rate information to a preset threshold, and respective RPE of the user corresponding to the result of the comparing.

29. An apparatus configured to provide exercise guide information, the apparatus comprising:
one or more processors; and
one or more memories including
an exercise history library, and computer readable instructions, which when executed by the one or more processors configure the one or more processors to:

iteratively generate the exercise history library, with respect to each of a plurality of previous order exercises performed by a user, to match exercise pattern information with corresponding RPE and biometric information of the previous order exercises, the exercise pattern information and the corresponding RPE and biometric information of the previous order exercises being generated by the one or more processors in corresponding generated exercise intensity information of the user respectively during the previous order exercises;

generate exercise pattern information from a detected exercise pattern of a user performing an exercise in a current order, where the exercise pattern information includes a measured exercise duration and measured exercise speed or measured movement of the user in the current order, where the measured exercise speed or measured movement is based on sensor data of a movement sensor measuring movement of the user;

search the exercise history library with respect to the generated exercise pattern, which is absent in the exercise history library, for stored exercise pattern information that matches the generated exercise pattern with at least a predetermined similarity or that is determined similar to the generated exercise pattern;

generate each of an estimated rate of perceived exertion (RPE) and an estimated biosignal based on information extracted from the exercise history library based on results of the search;

generate exercise intensity information of the user in the current order, the generating of the exercise intensity information in the current order comprises generating an evaluation score based on the estimated RPE, an estimated heart rate of the estimated biosignal, and a target heart rate, and generating the exercise intensity information in the current order based on the generated evaluation score;

generate exercise guide information based on the determined exercise intensity; and control provision of the generated exercise guide information to the user, wherein the controlled provision of the generated exercise guide information includes a selective control of output guidance to the user to change a current movement exertion by the user.

30. The apparatus of claim 29, further comprising:
an accelerometer, configured to measure movement information representative of the exercise speed of the user.

31. The apparatus of claim 29, wherein the apparatus is a wearable device.

32. A system configured to provide exercise guide information, the system comprising:

a wearable device configured to sense a biosignal that includes a heart rate of a user in an exercise of a current order, and to provide vibrational feedback to the user; and one or more processors configured to
receive the biosignal and a rate of perceived exertion (RPE), as indicated by the user, with respect to the exercise of the current order, determine a heart rate comparison result of a threshold consideration of a difference between the heart rate of the user and a target heart rate, adjust, based on respective predetermined variables, either one or both of the received RPE and the heart rate comparison result, determine an exercise intensity of the user in the current order based on an evaluation score determined based on both of the adjusted RPE and the adjusted heart rate comparison result, based on both of the adjusted received RPE and the heart rate comparison result, or based on both of the received RPE and the adjusted heart rate comparison result, and control the wearable device to implement the provision of the vibrational feedback to the user based on the determined exercise intensity corresponding to a movement pace of the user in the current order, wherein the control of the wearable device to implement the provision of the vibrational feedback includes controlling the wearable device to provide a first vibration based on a determination, by the one or more processors and dependent on the determined exercise intensity, to provide exercise guidance to increase the movement pace of the user, and controlling the wearable device to provide a second vibration based on a determination, by the one or more processors and dependent on the determined exercise intensity, to provide exercise guidance to decrease the movement pace of the user.

* * * * *